United States Patent
Ueda et al.

(10) Patent No.: US 10,000,791 B2
(45) Date of Patent: Jun. 19, 2018

(54) MEASUREMENT METHOD FOR HUMAN PANCREATIC LIPASE ACTIVITY

(71) Applicant: ASAHI KASEI PHARMA CORPORATION, Tokyo (JP)

(72) Inventors: Shigeru Ueda, Tokyo (JP); Shinichi Sakasegawa, Tokyo (JP)

(73) Assignee: ASAHI KASEI PHARMA CORPORATION, Tokyo (JP)

( * ) Notice: Subject to any disclaimer, the term of this patent is extended or adjusted under 35 U.S.C. 154(b) by 0 days. days.

(21) Appl. No.: 14/775,919

(22) PCT Filed: Apr. 17, 2014

(86) PCT No.: PCT/JP2014/060900
§ 371 (c)(1),
(2) Date: Sep. 14, 2015

(87) PCT Pub. No.: WO2014/171505
PCT Pub. Date: Oct. 23, 2014

(65) Prior Publication Data
US 2016/0024553 A1      Jan. 28, 2016

(30) Foreign Application Priority Data
Apr. 18, 2013   (JP) ................................ 2013-087665

(51) Int. Cl.
*C12Q 1/44*      (2006.01)

(52) U.S. Cl.
CPC ........... *C12Q 1/44* (2013.01); *G01N 2333/92* (2013.01)

(58) Field of Classification Search
CPC .............................. C12Q 1/44; G01N 2333/92
USPC ................................................... 435/19, 198
See application file for complete search history.

(56) References Cited

U.S. PATENT DOCUMENTS

| | | |
|---|---|---|
| 4,845,028 A | 7/1989 | Imamura et al. |
| 5,079,158 A | 1/1992 | Imamura et al. |
| 5,162,201 A | 11/1992 | Imamura et al. |
| 6,322,993 B1 | 11/2001 | Schelong et al. |
| 7,883,862 B2 | 2/2011 | Imamura et al. |
| 8,216,799 B2 | 7/2012 | Kageyama et al. |
| 8,288,117 B2 | 10/2012 | Nakamura et al. |
| 2008/0038765 A1 | 2/2008 | Imamura et al. |
| 2009/0011450 A1 | 1/2009 | Kageyama et al. |
| 2009/0093007 A1 | 4/2009 | Kageyama et al. |
| 2009/0246812 A1 | 10/2009 | Nakamura et al. |

FOREIGN PATENT DOCUMENTS

| | | |
|---|---|---|
| EP | 0285101 A | 10/1988 |
| JP | S59-91898 A | 5/1984 |
| JP | S63-245672 A | 10/1988 |
| JP | H03-228699 A | 10/1991 |
| JP | H11-504529 A | 4/1999 |
| JP | 2008-307048 A | 12/2008 |
| JP | 4836196 B2 | 12/2011 |

OTHER PUBLICATIONS

Andersson et al. Hydrolysis of Galactolipids by Human Pancreatic Lipolytic Enzymes and Duodenal Contents; Journal of Lipid Research, vol. 36 (1995) pp. 1392-1400.*
Hirano et al. Measurement of the Serum Lipoprotein Lipase Concentration Is Useful for Studying Triglyeride Metabolism: Comparison With Postheparin Plasma; Metabolism, vol. 53, No. 4 (2004) pp. 526-531.*
Fossati et al. Kinetic Colorimetric Assay of Lipase in Serum; Clinical Chemistry, vol. 38, No. 2 (1992) pp. 211-215.*
Christie, W. Diaglycerols: Structure, Composition, Function and Analysis; AOCS Lipid Libary (2017) downloaded from http://lipidlibrary.aocs.org/Primer/content.cfm?ItemNumber=39311 on Mar. 23, 2017.*
Norbert W. Tietz et al., "Lipase in Serum—the Elusive Enzyme: An Overview", Clinical Chemistry, 39, pp. 746-756, 1993.
Japanese Journal of Medicine and Pharmaceutical Science, vol. 41, No. 3, pp. 489-496, 1999.
C. Demanet et al., "Two Automated Fully Enzymatic Assays for Lipase Activity in Serum Compared: Positive Interference from Post-Heparin Lipase Activity", Clinical Chemistry, 38, pp. 288-292, 1992.
Norbert W. Tietz et al., "Lipase Activity Measured in Serum by a Continuous-Monitoring pH-Stat Technique—an Update", Clinical Chemistry, 35, p. 1688-1693, 1989.
Takayuki Uwajuma et al., "Formation and Purification of a New Enzyme Glycerol Oxidase and Stoichiometry of the Enzyme Reaction", Agricultural Biology and Chemistry, 44(2), pp. 399-406, 1980.
International Search Report issued with respect to application No. PCT/JP2014/060900, dated Jul. 15, 2014.

(Continued)

*Primary Examiner* — Scott Long
*Assistant Examiner* — Paul C Martin
(74) *Attorney, Agent, or Firm* — Greenblum & Bernstein, P.L.C.

(57) ABSTRACT

A measurement method for human pancreatic lipase activity in a sample, includes bringing a bile acid that makes a pH for giving a maximum value of human pancreatic lipase activity to be lower than 7.7, a diglyceride and a colipase into contact with the sample at pH 7.4 or lower; and detecting a signal amount varying in accordance with the human pancreatic lipase activity in the sample, and the bile acid is a bile acid containing: one of or two or more of a-type bile acids selected from the group consisting of GDCA, GCDCA, TDCA, TCDCA and salts thereof; and/or a combination of one of or two or more of b-1-type bile acids selected from the group consisting of GCA, GUDCA, TCA, TUDCA and salts thereof, and one of or two or more of b-2-type bile acids selected from the group consisting of DCA, CDCA and salts thereof.

25 Claims, 19 Drawing Sheets

(56) References Cited

OTHER PUBLICATIONS

International Preliminary Report on Patentability issued with respect to application No. PCT/JP2014/060900, dated Oct. 20, 2015.
Hideko Ishihara, "Effects of Bile Salts on Porcine Pancreatic Lipase-Catalyzed Lipolysis", The Journal of Hygienic Chemistry 21(6), p. 348-355, 1975.
Bengt Borgstrom et al., "Pancreatic Lipase and Co-Lipase, Interactions and Effects of Bile and Other Detergents", Eur.J.Biochemistry 37(60), p. 60-68, 1973.
European Search Report issued with respect to application No. 14784863.4, dated Jan. 14, 2016.
Maria Theresa Neves Petersen et al.,"How do lipases and esterases work: the electrostatic contribution", Journal of Biotechnology, vol. 85, No. 2, Feb. 13, 2001, pp. 115-147.

* cited by examiner

Fig. 10

| | LIQUITECH | CONTROLLED EXAMPLE | PRESENT EXAMPLE | | REFERENCE EXAMPLE | MEASURED VALUE/THEORETICAL VALUE | | | |
|---|---|---|---|---|---|---|---|---|---|
| | | | | | | CONTROLLED EXAMPLE | PRESENT EXAMPLE | | REFERENCE EXAMPLE |
| NON-CONJUGATED BILE SALT | | NaDCA(30mM) | NaDCA(20mM) | NaDCA(20mM) | NaDCA(20mM) | NaDCA(30mM) | NaDCA(20mM) | NaDCA(20mM) | NaDCA(20mM) |
| CONJUGATED BILE SALT | | NaTDCA(10mM) | NaGDCA(20mM) | NaGDCA(20mM) | NaGDCA(20mM) | NaTDCA(10mM) | NaGDCA(20mM) | NaGDCA(20mM) | NaGDCA(20mM) |
| pH | | pH7.95 | pH7.1 | pH7.4 | pH7.6 | pH7.95 | pH7.1 | pH7.4 | pH7.6 |
| | U/L | U/L | U/L | U/L | U/L | % | % | % | % |
| RECOMBINANT PANCREATIC LP-CONTAINING SERUM | 175.0 | 202.8 | 158.0 | 186.9 | 179.2 | 98.4 | 100.4 | 100.1 | 99.9 |
| PRECIPATH | 85.8 | 97.2 | 78.2 | 86.1 | 81.6 | 95.2 | 99.4 | 92.7 | 93.1 |
| PRECINORM | 53.3 | 50.2 | 40.1 | 48.4 | 43.9 | 78.2 | 80.3 | 82.5 | 80.9 |
| POOLED SERUM 1 | 40.0 | 44.8 | 37.7 | 43.1 | 39.1 | 92.0 | 98.7 | 96.3 | 96.4 |
| NORMAL SAMPLE 1 | 66.7 | 77.8 | 67.3 | 81.2 | 75.4 | 97.4 | 109.0 | 111.5 | 110.8 |
| 2 | 64.8 | 71.4 | 61.0 | 70.0 | 68.9 | 92.0 | 101.5 | 98.9 | 104.2 |
| 3 | 89.8 | 117.5 | 73.2 | 89.9 | 83.7 | 110.1 | 89.1 | 92.6 | 91.2 |
| 4 | 44.0 | 54.4 | 48.5 | 56.2 | 50.1 | 102.0 | 116.4 | 114.9 | 112.3 |
| 5 | 26.5 | 29.8 | 18.7 | 23.6 | 23.2 | 90.2 | 71.3 | 77.4 | 87.0 |
| 6 | 48.3 | 63.9 | 52.6 | 58.9 | 52.4 | 109.3 | 115.5 | 110.2 | 106.7 |
| 7 | 32.1 | 36.9 | 31.7 | 35.5 | 31.3 | 93.3 | 101.5 | 97.5 | 96.4 |
| 8 | 37.1 | 46.0 | 33.7 | 40.3 | 37.5 | 101.6 | 94.7 | 96.8 | 99.9 |
| 9 | 59.3 | 82.5 | 53.1 | 63.7 | 58.8 | 115.8 | 96.1 | 97.9 | 97.3 |
| 10 | 90.4 | 121.8 | 95.3 | 117.3 | 107.6 | 113.4 | 115.3 | 120.0 | 116.4 |
| HEPARIN-ADMINISTERED SAMPLE | 36.4 | 76.6 | 38.7 | 45.8 | 68.8 | 172.2 | 110.7 | 112.1 | 186.8 |
| 2 | 36.8 | 107.1 | 42.3 | 52.2 | 83.4 | 238.2 | 119.7 | 126.3 | 223.9 |
| 3 | 28.9 | 71.8 | 31.2 | 36.7 | 55.1 | 200.7 | 110.0 | 111.2 | 189.1 |
| 4 | 30.0 | 81.0 | 32.5 | 43.5 | 65.2 | 218.4 | 110.8 | 127.2 | 215.4 |
| 5 | 46.0 | 75.0 | 44.9 | 54.2 | 71.1 | 134.6 | 103.3 | 106.2 | 152.2 |
| 6 | 36.8 | 88.5 | 38.2 | 47.8 | 71.7 | 196.9 | 108.2 | 115.8 | 192.8 |
| 7 | 37.3 | 100.4 | 34.6 | 40.7 | 77.0 | 220.1 | 96.6 | 97.1 | 203.7 |
| 8 | 36.0 | 94.0 | 36.9 | 43.5 | 65.2 | 213.5 | 106.7 | 107.3 | 178.9 |
| 9 | 30.5 | 71.0 | 35.2 | 43.1 | 64.6 | 188.7 | 118.2 | 124.1 | 209.9 |
| AVERAGE (HEPARIN) | | | | | | 198.1 | 109.4 | 114.1 | 194.7 |

Fig. 11

| | | LOUITECH CONTROLLED SAMPLE PRESENT EXAMPLE | | | | | | | MEASURED VALUE/THEORETICAL VALUE(%) CONTROLLED SAMPLE PRESENT EXAMPLE | | | | | |
|---|---|---|---|---|---|---|---|---|---|---|---|---|---|---|
| NON-CONJUGATED BILE SALT | | NaDCA(30) | NaDCA(20) | NaGDCA(20) | NaDCA(13.3) | | NaTDCA(20) | NaGCA(20) | | NaDCA(20) | NaDCA(20) | NaDCA(13.3) | NaTDCA(20) | NaTDCA(20) |
| CONJUGATED BILE SALT | | NaTDCA(10) | | | NaDCA(13.3) | | NaTDCA(20) | NaGCA(20) | | NaTDCA(10) | | NaDCA(13.3) | NaTDCA(20) | NaGCA(20) |
| pH | | 7.95 | 6.9 | 6.9 | 6.9 | | 6.9 | 6.9 | | 7.95 | 6.9 | 6.9 | 6.9 | 6.9 |
| | | U/L | U/L | U/L | U/L | | U/L | U/L | | % | % | % | % | % |
| α-KETOGLUTARIC SERUM | 174.4 | 202.0 | 111.7 | | 138.5 | | 227.8 | 227.2 | | 99.4 | 101.4 | 100.5 | 97.9 | 98.5 |
| PRECIPATH | 110.3 | 131.3 | 87.1 | | 87.3 | | 157.7 | 155.2 | | 103.0 | 97.9 | 101.1 | 107.6 | 106.6 |
| PRECINORM | 53.3 | 50.2 | 27.2 | | 34.3 | | 61.5 | 58.3 | | 86.1 | 86.3 | 84.6 | 87.6 | 83.3 |
| POOLED SERUM 1 | 40.0 | 43.8 | 25.0 | | 31.5 | | 53.8 | 53.2 | | 103.4 | 109.2 | 106.5 | 102.3 | 105.2 |
| POOLED SERUM 2 | 19.0 | 19.0 | 10.7 | | 15.3 | | 24.0 | 26.0 | | 118.9 | 124.9 | 123.0 | 105.0 | 112.0 |
| HEPARIN 11 | 39.6 | 34.0 | 22.6 | | 34.3 | | 63.1 | 62.9 | | 224.5 | 90.3 | 118.0 | 121.7 | 121.2 |
| 12 | 51.8 | 92.3 | 27.6 | | 33.1 | | 63.5 | 58.5 | | 163.3 | 90.0 | 84.1 | 93.1 | 85.9 |
| 13 | 38.5 | 99.2 | 22.4 | | 22.8 | | 65.3 | 59.3 | | 244.4 | 102.3 | 79.5 | 129.6 | 117.6 |
| 14 | 33.6 | 64.7 | 19.6 | | 21.6 | | 46.0 | 42.1 | | 186.1 | 104.8 | 87.2 | 105.0 | 95.7 |
| | | | | | | | AVERAGE HEPARIN SAMPLE | | | 204.5 | 99.3 | 91.7 | 112.3 | 105.1 |

Fig. 12

| | CONTROLLED EXAMPLE | PRESENT EXAMPLE | PRESENT EXAMPLE | PRESENT EXAMPLE | CONTROLLED EXAMPLE | PRESENT EXAMPLE | PRESENT EXAMPLE |
|---|---|---|---|---|---|---|---|
| | | | | | MEASURED VALUE/THEORETICAL VALUE | | |
| SURFACE ACTIVE AGENT | NPE | NPE | ADEKA TOL TN-100 | ADEKA TOL TN-100 | NPE | NPE | ADEKA TOL TN-100 |
| NON-CONJUGATED BILE SALT | NaDCA(30mM) | NaGDCA(20mM) | NaGDCA(20mM) | NaGDCA(20mM) | NaDCA(30mM) | NaGDCA(20mM) | NaGDCA(20mM) |
| CONJUGATED BILE SALT | NaTDCA(10mM) | | NaTDCA(20mM) | NaTDCA(20mM) | NaTDCA(10mM) | NaTDCA(20mM) | NaTDCA(20mM) |
| pH | pH7.95 | pH7.2 | pH7.4 | pH7.2 | pH7.95 | pH7.2 | pH7.4 |
| | U/L | U/L | U/L | U/L | % | % | % |
| HEPARIN-ADMINISTERED SAMPLE A | 74.2 | 40.0 | 41.3 | 28.3 | 209.5 | 116.3 | 118.1 |
| HEPARIN-ADMINISTERED SAMPLE B | 97.2 | 74.0 | 61.2 | 51.9 | 150.2 | 111.7 | 106.6 |

| | PRESENT EXAMPLE |
|---|---|
| SURFACE ACTIVE AGENT | ADEKA TOL TN-100 |
| NON-CONJUGATED BILE SALT | NaGDCA(20mM) |
| CONJUGATED BILE SALT | NaTDCA(20mM) |
| pH | pH7.4 |
| | % |
| HEPARIN-ADMINISTERED SAMPLE A | 101.5 |
| HEPARIN-ADMINISTERED SAMPLE B | 110.1 |

MEASUREMENT METHOD FOR HUMAN PANCREATIC LIPASE ACTIVITY

TECHNICAL FIELD

The present invention relates to a method and a kit for measuring human pancreatic lipase activity in a sample in the field of laboratory testing.

BACKGROUND ART

A human pancreatic lipase is significant as a diagnostic marker for a pancreatic disease such as acute pancreatitis, and a reagent for measuring the enzyme activity in serum is commercially available as a laboratory test reagent. The optimum hydrogen ion exponent (pH) at the time of the measurement of the enzyme activity depends on a substrate or a reaction condition to be employed, but is reported to be in a range of about 7.5 to 10 (see, for example, Non Patent Literature 1). Enzymatic characteristics of the human pancreatic lipase include that the reaction occurs on an interface of an emulsion or a micelle containing a substrate, and that a bile acid and a protein having a molecular weight of approximately 1 lkDa designated as a colipase are necessary for activating the enzyme. If a bile acid and a colipase are absent, the active center of the pancreatic lipase is covered with a domain designated as lid meaning a cover and hence cannot come into contact with a substrate. The bile acid influences formation of an emulsion or a micelle. In addition, the conformation of the human pancreatic lipase is changed if the colipase is additionally present, and the active center of the human pancreatic lipase can bound to a substrate, which can activate the human pancreatic lipase. Thus, it is known that a human pancreatic lipase acts on an interface of a complex containing a hydrophobic substrate, a bile salt and a colipase.

In the measurement of the activity of a human pancreatic lipase in a sample, a triglyceride is conventionally used as the substrate. The triglyceride is used in the form of what is called an emulsion in which it is emulsified and dispersed in a buffer solution by force stirring together with gum arabic, polyvinyl alcohol or the like. In measuring the lipase activity by using a triglyceride substrate, for example, a fatty acid produced through a lipase reaction is quantitatively determined by alkalimetry. Alternatively, an attempt has been made to measure a fatty acid released from a triglyceride substrate through a lipase reaction by an enzymatic method, but it is difficult to spectroscopically measure the lipase activity by using an enzyme conjugated system because the triglyceride substrate shows strong turbidity due to the emulsion. Besides, an emulsion substrate has a disadvantage that phase separation easily occurs during storage, and it is difficult to measure the lipase activity with high reproducibility. In order to solve these problems of the methods using a triglyceride substrate, a method in which a diglyceride is used as a substrate (see, for example, Patent Literatures 1 and 2) and a method in which a synthetic substrate is used (see, for example, Non Patent Literature 2) have been developed, and these methods are currently employed in a routine laboratory testing.

As an advantage of using a diglyceride as a substrate, since a diglyceride is more hydrophilic than a triglyceride, the substrate can be made clear when used in combination with a surface active agent, and hence such a substrate can be conveniently used in a general purpose automatic analyzer.

As a diglyceride substrate, 1,2-diglyceride is principally used. It is known that 1,2-diglyceride is changed into 1,3-diglyceride in a molecule through a transfer reaction of an ester bond, and hence it is used with this change suppressed as much as possible. Besides, it has been proposed that a part of 1,2-diglyceride is converted into 1,3-diglyceride, and the resultant mixture is stabilized in the form of a liquid to be used as a substrate for measuring a human pancreatic lipase (see, for example, Patent Literature 3). Here, it has been reported that a measurement method using a diglyceride substrate is influenced by a non-pancreatic lipase such as a lipoprotein lipase or a hepatic lipase. It has been also reported that the measurement method using a diglyceride substrate has a harmful effect that the specificity to a pancreatic lipase is easily lowered because this method is influenced by a non-pancreatic lipase, such as a lipoprotein lipase, or an esterase contained in blood (see, for example, Patent Literature 4). A non-pancreatic lipase such as a human lipoprotein lipase or hepatic lipase is released into blood by heparin. Therefore, the pancreatic lipase activity in blood cannot be accurately measured in a sample to which heparin has been administered. On the other hand, it is regarded that a routine test reagent for measuring human pancreatic lipase activity using a synthetic substrate is not influenced by a non-pancreatic lipase such as a lipoprotein lipase or a hepatic lipase (see, for example, Non Patent Literature 2), but there is a problem in stability of the synthetic substrate in a weak alkaline region corresponding to the optimum pH of the lipase.

As a method for avoiding the influence of a non-pancreatic lipase, it has been reported that the influence of a non-pancreatic lipase is reduced, in using a commercially available kit for measuring lipase activity using 1,2-dilinoleoyl glycerol, that is, a diglyceride, as the substrate, by replacing sodium deoxycholate used as a bile salt with sodium glycocholate (see, for example, Non Patent Literature 3), but the details are unknown. Besides, not only the measurement method for lipase activity using a diglyceride as a substrate but also a measurement method for lipase activity using a triglyceride as a substrate is influenced by a non-pancreatic lipase, and it has been reported also with respect to this case that the influence of a non-pancreatic lipase can be avoided by replacing deoxycholic acid with glycocholic acid (see, for example, Non Patent Literature 4). However, it is still difficult to measure lipase activity with high reproducibility because a triglyceride substrate has disadvantages that it cannot be spectroscopically measured and phase separation is easily caused during storage as described above.

CITATION LIST

Patent Literature

Patent Literature 1: Japanese Patent Laid-Open No. 59-91898 (Japanese Patent No. 1607890)
Patent Literature 2: Japanese Patent Laid-Open No. 63-245672
Patent Literature 3: Japanese Patent No. 4836196
Patent Literature 4: Japanese Patent Laid-Open No. 2008-307048

Non Patent Literature

Non Patent Literature 1: Clinical Chemistry, 39: pp. 746-756, 1993

Non Patent Literature 2: Japanese Journal of Medicine and Pharmaceutical Science, Vol. 41, No. 3, pp. 489-496, 1999

Non Patent Literature 3: Clinical Chemistry, 38: 288-292, 1992

Non Patent Literature 4: Clinical Chemistry, 35: pp. 1688-1693, 1989

Non Patent Literature 5: Agricultural Biology and Chemistry, 44(2), 399-406, 1980

SUMMARY OF INVENTION

Technical Problem

A measurement method for human pancreatic lipase activity in a sample using a diglyceride as a substrate is better in the reproducibility than a measurement method using a triglyceride, but is relatively easily influenced by a lipoprotein lipase or a hepatic lipase. Accordingly, there is a demand for a measurement method for human pancreatic lipase activity that can attain higher specificity to pancreatic lipase while using a diglyceride as a substrate, and avoiding the influence.

Solution to Problem

As described above, the optimum pH in measuring human pancreatic lipase activity depends upon a substrate and a reaction condition to be employed in general, but is reported to fall in a range of about 7.5 to 10. The present inventors have found, as a result of earnest examinations, that the influence of a non-pancreatic lipase such as a lipoprotein lipase or a hepatic lipase, which can be mixed in a sample due to administration of heparin or the like, can be unexpectedly reduced, in the measurement of human pancreatic lipase activity in a sample using a diglyceride as a substrate, by moving a pH for giving a maximum value of human pancreatic lipase activity to the acidic side, and performing a human pancreatic lipase reaction under coexistence of a bile acid and a colipase under a pH condition lower than that conventionally reported.

Specifically, the present invention provides a measurement method for human pancreatic lipase activity with influence of a non-pancreatic lipase reduced in which a specific conjugated bile acid is singly used or used in combination with another bile acid to make a pH for giving a maximum value of the human pancreatic lipase activity to be lower than 7.7, and the human pancreatic lipase activity in a sample is measured at pH 7.4 or lower.

It is noted that the "conjugated bile acid" refers to a bile acid conjugated with an amino acid such as glycine or taurine, and a "non-conjugated bile acid" means a bile acid excluding conjugated bile acids. Besides, the "optimum pH" means a measurement pH at which the pancreatic lipase activity is the maximum.

One aspect of the present invention is a measurement method for human pancreatic lipase activity in a sample, which includes 1) a contact step of bringing a bile acid that makes a pH for giving a maximum value of the human pancreatic lipase activity to be lower than 7.7, a diglyceride and a colipase into contact with the sample at pH 7.4 or lower; and 2) a detection step of detecting a signal amount varying in accordance with the human pancreatic lipase activity in the sample, in which the bile acid that makes the pH for giving a maximum value of human pancreatic lipase activity to be lower than 7.7 is a bile acid containing: a) one of or two or more of a-type bile acids selected from the group consisting of glycodeoxycholic acid (GDCA), glycochenodeoxycholic acid (GCDCA), taurodeoxycholic acid (TDCA), taurochenodeoxycholic acid (TCDCA), and salts thereof; and/or b) a combination of one of or two or more of b-1-type bile acids selected from the group consisting of glycocholic acid (GCA), glycoursodeoxycholic acid (GUDCA), taurocholic acid (TCA), tauroursodeoxycholic acid (TUDCA) and salts thereof, and one of or two or more of b-2-type bile acids selected from the group consisting of deoxycholic acid (DCA), chenodeoxycholic acid (CDCA) and salts thereof.

In plotting the human pancreatic lipase activity against pH, for example, if an upward convex curve is drawn, a maximum value of the activity means the peak of the activity. Besides, while the "optimum pH" means the measurement pH at which the human pancreatic lipase activity is the maximum under usual conditions, a measurement pH at which the human pancreatic lipase activity is the maximum in the presence of the above-described bile acid will be designated as an "apparent optimum pH" in some cases.

For example, if the a-type bile acid(s) is used in the contact step, an addition rate of the a-type bile acid(s) is 40% or more based on a total amount of all bile acids and/or salts thereof.

A non-ionic surface active agent may be present together with the diglyceride. The non-ionic surface active agent is, for example, at least one selected from the group consisting of polyoxyethylene alkyl ether, polyoxyethylene alkyl phenyl ether, and polyoxyethylene secondary alcohol ether.

In the detection step, for example, a colorimetric method is employed. Besides, in the contact step, for example, the concentration of all bile acids is ten times or more as high as that of the glyceride in terms of a molar ratio. Furthermore, in the contact step, for example, the pH is 7.2 or lower.

Exemplified features of the present invention are:

(1)

A measurement method for human pancreatic lipase activity in a sample, comprising:

1) a contact step of bringing a bile acid that makes a pH for giving a maximum value of human pancreatic lipase activity to be lower than 7.7, a diglyceride and a colipase into contact with the sample at pH 7.4 or lower; and 2) a detection step of detecting a signal amount varying in accordance with the human pancreatic lipase activity in the sample, wherein the bile acid is a bile acid containing:

a) one of or two or more of a-type bile acids selected from the group consisting of glycodeoxycholic acid (GDCA), glycochenodeoxycholic acid (GCDCA), taurodeoxycholic acid (TDCA), taurochenodeoxycholic acid (TCDCA) and salts thereof; and/or b) a combination of one of or two or more of b-1-type bile acids selected from the group consisting of glycocholic acid (GCA), glycoursodeoxycholic acid (GUDCA), taurocholic acid (TCA), tauroursodeoxycholic acid (TUDCA) and salts thereof, and one of or two or more of b-2-type bile acids selected from the group consisting of deoxycholic acid (DCA), chenodeoxycholic acid (CDCA) and salts thereof.

(2)

The measurement method according to (1), in which the sample is a sample which may be contaminated with a human non-pancreatic lipase, or a sample which can contain a human non-pancreatic lipase.

(3)

The measurement method according to (1) or (2), wherein the bile acid(s) of a) is used in the contact step.

(4)
The measurement method according to any one of (1) to (3), wherein when the bile acid(s) of a) is used, an addition rate of the a-type bile acid(s) is 40% or more based on a total amount of all bile acids and/or salts thereof.

(5)
The measurement method according to (1) or (2), wherein the bile acid(s) of b) is used in the contact step.

(6)
The measurement method according to any one of (1) to (4), wherein the a-type bile acid(s) is one or two selected from glycodeoxycholic acid (GDCA) and salts thereof.

(7)
The measurement method according to any one of (1) to (4), wherein the a-type bile acid(s) is one, or two or more selected from the group consisting of glycodeoxycholic acid (GDCA), taurodeoxycholic acid (TDCA) and salts thereof.

(8)
The measurement method according to any one of (1) to (4), wherein the a-type bile acid(s) is one or two selected from taurodeoxycholic acid (TDCA) and salts thereof.

(9)
The measurement method according to any one of (1) to (8), wherein a non-ionic surface active agent is present together with the diglyceride.

(10)
The measurement method according to (9), wherein the non-ionic surface active agent is at least one selected from the group consisting of polyoxyethylene alkyl ether, polyoxyethylene alkyl phenyl ether, and polyoxyethylene secondary alcohol ether.

(11)
The measurement method according to any one of (1) to (10), wherein a colorimetric method is employed in the detection step.

(12)
The measurement method according to any one of (1) to (11), wherein a concentration of all bile acids is ten times or more as high as a concentration of the diglyceride in terms of a molar ratio in the contact step.

(13)
The measurement method according to any one of (1) to (12), wherein the pH is 7.2 or lower in the contact step.

(14)
A kit for measuring human pancreatic lipase activity in a sample, at least comprising a bile acid that makes a pH for giving a maximum value of human pancreatic lipase activity to be lower than 7.7, a diglyceride and a colipase,
wherein a pH at the time of measurement of the human pancreatic lipase activity is adjusted to 7.4 or lower, and
the bile acid is a bile acid containing:
a) one of or two or more of a-type bile acids selected from the group consisting of glycodeoxycholic acid (GDCA), glycochenodeoxycholic acid (GCDCA), taurodeoxycholic acid (TDCA), taurochenodeoxycholic acid (TCDCA) and salts thereof; and/or
b) a combination of one of or two or more of b-1-type bile acids selected from the group consisting of glycocholic acid (GCA), glycoursodeoxycholic acid (GUDCA), taurocholic acid (TCA), tauroursodeoxycholic acid (TUDCA) and salts thereof, and one of or two or more of b-2-type bile acids selected from the group consisting of deoxycholic acid (DCA), chenodeoxycholic acid (CDCA) and salts thereof.

(15)
The kit according to (14), wherein the sample is a sample which may be contaminated with a human non-pancreatic lipase, or a sample which can contain a human non-pancreatic lipase.

(16)
The kit according to (14) or (15), further comprising a chromogen.

(17)
The kit according to (14) to (16), wherein the pH at the time of the measurement of the activity is adjusted to 7.2 or lower.

(18)
The kit according to any one of (14) to (17), wherein contents are stored dividedly in a plurality of vessels.

(19)
A measurement method for human pancreatic lipase activity in a sample, comprising:
1) a contact step of bringing a bile acid, a diglyceride and a colipase into contact with the sample at pH 7.4 or lower; and
2) a detection step of detecting a signal amount varying in accordance with the human pancreatic lipase activity in the sample,
wherein a concentration of the diglyceride is 0.35 to 2.5 mmol/L, and a concentration of the bile acid is ten to twenty times as high as the concentration of the diglyceride in terms of a molar ratio, and
the bile acid is:
a) a bile acid containing one of or two or more of a-type bile acids selected from the group consisting of glycodeoxycholic acid (GDCA), glycochenodeoxycholic acid (GCDCA), taurodeoxycholic acid (TDCA), taurochenodeoxycholic acid (TCDCA) and salts thereof, a molar ratio of the a-type bile acid(s) being 40% or more based on a total amount of all bile acids and/or salts thereof; and/or
b) a bile acid containing a combination of one of or two or more of b-1-type bile acids selected from the group consisting of glycocholic acid (GCA), glycoursodeoxycholic acid (GUDCA), taurocholic acid (TCA), tauroursodeoxycholic acid (TUDCA) and salts thereof, and one of or two or more of b-2-type bile acids selected from the group consisting of deoxycholic acid (DCA), chenodeoxycholic acid (CDCA) and salts thereof, a molar ratio of the b-1-type bile acid(s) being 30 to 70% based on the total amount of all the bile acids and/or salts thereof.

(20)
The measurement method according to (19), wherein the sample is a sample which may be contaminated with a human non-pancreatic lipase, or a sample which can contain a human non-pancreatic lipase.

(21)
The measurement method according to (19) or (20), wherein the bile acid(s) of a) is used in the contact step.

(22)
The measurement method according to (19) or (20), wherein the bile acid(s) of b) is used in the contact step.

(23)
The measurement method according to any one of (19) to (21), wherein the a-type bile acid(s) is one or two selected from glycodeoxycholic acid (GDCA) and salts thereof.

(24)
The measurement method according to any one of (19) to (21), wherein the a-type bile acid(s) is one, or two or more selected from the group consisting of glycodeoxycholic acid (GDCA), taurodeoxycholic acid (TDCA) and salts thereof.

(25)

The measurement method according to any one of (19) to (21), wherein the a-type bile acid(s) is one or two selected from taurodeoxycholic acid (TDCA) and salts thereof.

(26)

The measurement method according to any one of (19) to (25), wherein a non-ionic surface active agent is present together with the diglyceride.

(27)

The measurement method according to (26), wherein the non-ionic surface active agent is at least one selected from the group consisting of polyoxyethylene alkyl ether, polyoxyethylene alkyl phenyl ether, and polyoxyethylene secondary alcohol ether.

(28)

The measurement method according to any one of (19) to (27), wherein a colorimetric method is employed in the detection step.

(29)

The measurement method according to any one of (19) to (28), wherein the pH is 7.2 or lower in the contact step.

(30)

A kit for measuring human pancreatic lipase activity in a sample, at least comprising a bile acid, a diglyceride and a colipase, wherein a pH at the time of measurement of the human pancreatic lipase activity is adjusted to 7.4 or lower, a concentration of the diglyceride in a reaction solution in which at least the bile acid, the glyceride and the colipase are brought into contact with the sample is 0.35 to 2.5 mmol/L, and t a concentration of the bile acid is adjusted to ten to twenty times as high as the concentration of the diglyceride in terms of a molar ratio, and the bile acid is:

a) a bile acid containing one of or two or more of a-type bile acids selected from the group consisting of glycodeoxycholic acid (GDCA), glycochenodeoxycholic acid (GCDCA), taurodeoxycholic acid (TDCA), taurochenodeoxycholic acid (TCDCA) and salts thereof, a molar ratio of the a-type bile acid(s) being 40% or more based on a total amount of all bile acids and/or salts thereof; and/or b) a bile acid containing a combination of one or two or more of b-1-type bile acids selected from the group consisting of glycocholic acid (GCA), glycoursodeoxycholic acid (GUDCA), taurocholic acid (TCA), tauroursodeoxycholic acid (TUDCA) and salts thereof, and one of or two or more of b-2-type bile acids selected from the group consisting of deoxycholic acid (DCA), chenodeoxycholic acid (CDCA) and salts thereof, a molar ratio of the b-1-type bile acid(s) being 30 to 70% based on the total amount of all the bile acids and/or salts thereof.

(31)

The measurement method according to (30), wherein the sample is a sample which may be contaminated with a human non-pancreatic lipase, or a sample which can contain a human non-pancreatic lipase.

(32)

The kit according to (30) or (31), further comprising a chromogen.

(33)

The kit according to any one of (30) to (32), wherein a pH at the time of the measurement of the activity is adjusted to 7.2 or lower.

(34)

The kit according to any one of (30) to (33), wherein contents are stored dividedly in a plurality of vessels.

Another aspect of the present invention is a kit for measuring human pancreatic lipase activity in a sample that at least contains a bile acid that makes a pH for giving a maximum value of human pancreatic lipase activity to be lower than 7.7, a diglyceride and a colipase, in which a pH at the time of measurement of the human pancreatic lipase activity is adjusted to 7.4 or lower, and the bile acid that makes the pH for giving the maximum value of the human pancreatic lipase activity to be lower than 7.7 is a bile acid containing: a) one of or two or more of a-type bile acids selected from the group consisting of glycodeoxycholic acid (GDCA), glycochenodeoxycholic acid (GCDCA), taurodeoxycholic acid (TDCA), taurochenodeoxycholic acid (TCDCA) and salts thereof; and/or b) a combination of one of or two or more of b-1-type bile acids selected from the group consisting of glycocholic acid (GCA), glycoursodeoxycholic acid (GUDCA), taurocholic acid (TCA), tauroursodeoxycholic acid (TUDCA) and salts thereof, and one of or two or more of b-2-type bile acids selected from the group consisting of deoxycholic acid (DCA), chenodeoxycholic acid (CDCA) and salts thereof.

The kit may further contain a chromogen. In the kit, a pH at the time of the activity measurement is adjusted pH 7.2 or lower. In the kit, contents may be stored dividedly in a plurality of vessels.

Alternatively, another aspect of the present invention is a measurement method for human pancreatic lipase activity in a sample, including:

1) a contact step, performed at least under conditions i) below, of bringing ii) a diglyceride and iii) a colipase into contact with the sample into contact at pH 7.4 or lower, the conditions i) including the following a) and/or b):

a) one of or two or more of conjugated bile acids (a-type bile acids) selected from the group consisting of glycodeoxycholic acid (GDCA), glycochenodeoxycholic acid (GCDCA), taurodeoxycholic acid (TDCA), taurochenodeoxycholic acid (TCDCA), and salts thereof is involved, an apparent optimum pH in measuring the human pancreatic lipase activity can be measured, and the bile acid(s) is present in the contact step under a condition for making the apparent optimum pH to be lower than 7.7; and b) a conjugated bile acid (a b-1-type bile acid) described in b-1) below and a non-conjugated bile acid (a b-2-type bile acid) described in b-2) below are both present at least at the time of measurement in the contact step under a condition where a presence proportion (a molar proportion) of the b-1-type bile acid to all bile acids (including salts thereof) is 30% or more and 70% or less:

b-1) one of or two or more of b-1-type bile acids selected from the group consisting of glycocholic acid (GCA), glycoursodeoxycholic acid (GUDCA), taurocholic acid (TCA), tauroursodeoxycholic acid (TUDCA) and salts thereof; and b-2) one of or two or more of b-2-type bile acids selected from the group consisting of deoxycholic acid (DCA), chenodeoxycholic acid (CDCA) and salts thereof;

and 2) a detection step of detecting a signal amount varying in accordance with the human pancreatic lipase activity in the sample.

For example, i) described above is a) described above. Besides, for example, in a) described above, an addition rate of the a-type bile acid(s) is 40% or more based on a total amount of bile acids and/or salts thereof. Alternatively, i) described above is b) described above.

For example, the a-type bile acid(s) is glycodeoxycholic acid (GDCA). Alternatively, the a-type bile acid(s) is glycodeoxycholic acid (GDCA) and taurodeoxycholic acid (TDCA).

For example, ii) described above is a mixture with a non-ionic surface active agent. Examples of the non-ionic surface active agent include polyoxyethylene alkyl ether, polyoxyethylene alkyl phenyl ether and polyoxyethylene secondary alcohol ether.

For example, 2) described above is performed by a colorimetric method.

For example, a concentration of i) described above is ten times or more as high as that of the diglyceride in terms of a molar ratio.

For example, the sample is brought into contact at pH 7.2 or lower.

Alternatively, a still another aspect of the present invention is a composition for measuring human lipase activity in a sample that at least contains i) described below, ii) a diglyceride and iii) a colipase, and is prepared to have pH 7.4 or lower at the time of activity measurement, i) including the following a) and/or b):

a) a bile acid containing one of or two or more of a-type bile acids selected from the group consisting of glycodeoxycholic acid (GDCA), glycochenodeoxycholic acid (GCDCA), taurodeoxycholic acid (TDCA), taurochenodeoxycholic acid (TCDCA) and salts thereof, and having a measurable apparent optimum pH in measuring the pancreatic lipase activity of lower than 7.7; and b) a bile acid containing both a b-1-type bile acid described in b-1) below and a b-2-type bile acid described in b-2) below, and having a presence proportion (a molar proportion) of the b-1-type bile acid to all bile acids (including salts thereof) of 30% or more and 70% or less:

b-1) one of or two or more of b-1-type bile acids selected from the group consisting of glycocholic acid (GCA), glycoursodeoxycholic acid (GUDCA), taurocholic acid (TCA), tauroursodeoxycholic acid (TUDCA) and salts thereof; and b-2) one of or two or more of b-2-type bile acids selected from the group consisting of deoxycholic acid (DCA), chenodeoxycholic acid (CDCA) and salts thereof.

For example, the composition contains a chromogen. Besides, for example, the composition is prepared to have pH 7.2 or lower at the time of the activity measurement. The composition may be in the form of a kit divided into a plurality of elements.

Advantageous Effects of Invention

The present invention can provide a measurement method for human pancreatic lipase activity in a sample using a diglyceride as a substrate, in which influence of a non-pancreatic lipase such as a lipoprotein lipase or a hepatic lipase is reduced and high reproducibility is exhibited.

BRIEF DESCRIPTION OF DRAWINGS

FIG. 10 is a table showing results obtained in Example 8.
FIG. 11 is a table showing results obtained in Example 9.
FIG. 12 is a table showing results obtained in Example 10.

DESCRIPTION OF EMBODIMENTS

Figure 1:
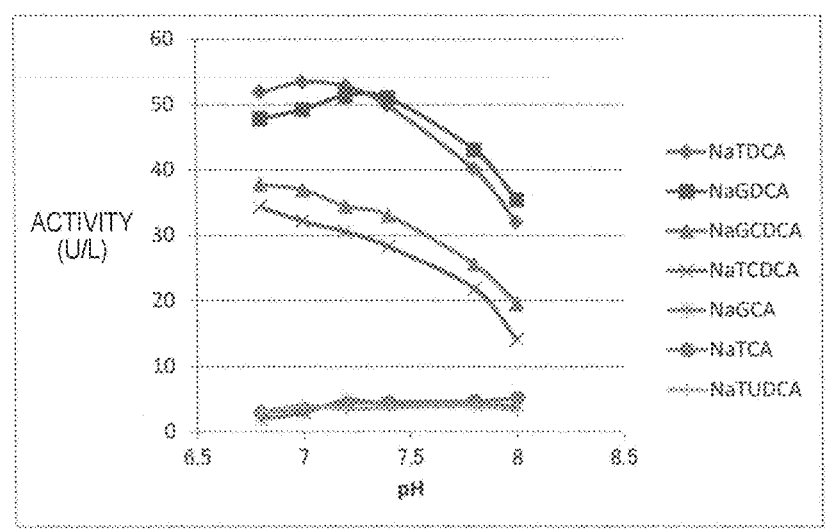
FIG. 1 is a graph illustrating pH dependence of human pancreatic lipase activity in the presence of a sodium salt of a conjugated bile acid according to Example 1.

An embodiment of the present invention will now be described. It is, however, noted that the following embodiment of the present invention is not intended to limit the invention. Various alternative forms, examples and operation techniques will become apparent for those skilled in the art from the present disclosure. It is to be understood that the present invention embraces variously modified embodiments and the like not described herein.

A measurement method for human pancreatic lipase activity in a sample according to the embodiment is a method including: 1) a contact step of bringing a bile acid that makes a pH for giving a maximum value of human pancreatic lipase activity to be lower than 7.7, and preferably 7.4 or lower, a diglyceride and a colipase into contact with the sample at pH 7.4 or lower; and 2) a detection step of detecting a signal amount varying in accordance with the human pancreatic lipase activity in the sample.

Here, the bile acid that makes a pH for giving a maximum value of the human pancreatic lipase activity to be lower than 7.7, and preferably 7.4 or lower is a bile acid containing: a) one of or two or more of conjugated bile acids, that is, a-type bile acids, selected from the group consisting of glycodeoxycholic acid (GDCA), glycochenodeoxycholic acid (GCDCA), taurodeoxycholic acid (TDCA), taurochenodeoxycholic acid (TCDCA) and salts thereof.

Alternatively, the bile acid that makes a pH for giving a maximum value of the human pancreatic lipase activity to be lower than 7.7, and preferably 7.4 or lower is a bile acid containing: b) a combination of one of or two or more of b-1-type bile acids, conjugated bile acids, selected from the group consisting of glycocholic acid (GCA), glycoursodeoxycholic acid (GUDCA), taurocholic acid (TCA), taurursodeoxycholic acid (TUDCA) and salts thereof, and one of or two or more of b-2-type bile acids, non-conjugated bile acids, selected from the group consisting of deoxycholic acid (DCA), chenodeoxycholic acid (CDCA) and salts thereof.

Alternatively, the bile acid that makes a pH for giving a maximum value of the human pancreatic lipase activity to be lower than 7.7, and preferably 7.4 or lower is a bile acid containing an a-type bile acid and a combination of a b-1-type bile acid and a b-2-type bile acid.

As the sample to be measured for the human pancreatic lipase activity, any sample can be used as long as it contains a human pancreatic lipase, and is preferably human blood, and more preferably human serum.

The a-type bile acid is preferably one, or two or more selected from the group consisting of glycodeoxycholic acid (GDCA), glycochenodeoxycholic acid (GCDCA), taurodeoxycholic acid (TDCA) and salts thereof. Alternatively, the a-type bile acid is preferably one, or two or more selected from the group consisting of glycodeoxycholic acid (GDCA), taurodeoxycholic acid (TDCA), taurochenodeoxycholic acid (TCDCA) and salts thereof.

Further alternatively, the a-type bile acid is preferably one, or two or more selected from the group consisting of glycodeoxycholic acid (GDCA), glycochenodexoycholic acid (GCDCA), taurochenodeoxycholic acid (TCDCA) and salts thereof. Further alternatively, the a-type bile acid is preferably one, or two or more selected from the group consisting of taurodeoxycholic acid (TDCA), glycochenodeoxycholic acid (GCDCA), taurochenodeoxycholic acid (TCDCA) and salts thereof.

The a-type bile acid is more preferably one, or two or more selected from the group consisting of glycodeoxycholic acid (GDCA), taurodeoxycholic acid (TDCA) and salts thereof. Accordingly, a more preferable a-type bile acid is a combination of glycodeoxycholic acid (GDCA) or a salt thereof and taurodeoxycholic acid (TDCA) or a salt thereof; glycodeoxycholic acid (GDCA) or a salt thereof; or taurodeoxycholic acid (TDCA) or a salt thereof. Further preferably, the a-type bile acid is one or two selected from glycodeoxycholic acid (GDCA) and salts thereof, or one or two selected from taurodeoxycholic acid (TDCA) and salts thereof.

The a-type bile acid may be used together with another bile acid. In this case, the presence proportion (molar ratio) of the a-type bile acid is preferably 40% or more based on the total amount of the bile acids and/or salts thereof. If the presence proportion (molar proportion) of the a-type bile acid is lower than 40%, an effect to move the pH for giving a maximum value of the human pancreatic lipase activity to the acid side tends to be reduced.

If the combination of the b-1-type bile acid and the b-2-type bile acid is employed, the presence proportion (molar proportion) of the b-1-type bile acid to all the bile acids (including salts thereof) is preferably 30% or more and 70% or less. If the presence proportion (molar ratio) of the b-1-type bile acid is lower than 30%, a pancreatic lipase activation proportion attained by addition of the colipase tends to be lowered, and if it exceeds 70%, the sensitivity in the activation measurement tends to be lowered.

In measuring the human pancreatic lipase activity in a sample, the total amount of bile acids in a reaction solution is, for example, 8 mmol/L or more. Besides, the concentration of all the bile acids including the salts thereof is, in terms of a molar ratio, preferably ten times or more and twenty times or less, and more preferably twelve times or more and twenty times or less as high as the concentration of the diglyceride. If the concentration is lower than ten times as high as that of the diglyceride, the intensity of the lipase activity tends to be insufficient. If the concentration is more than twenty times as high as that of diglyceride, the total bile salt concentration and the sensitivity are in a relationship corresponding to a saturation curve at a given concentration of the diglyceride, and hence, the sensitivity tends to be gradually lowered. The a-type bile acid, the b-1-type bile acid and the b-2-type bile acid are available from, for example, Sigma-Aldrich and the like. It is noted that the concentration of the diglyceride is preferably a concentration described later.

The pH at the time of the lipase activity measurement is 7.4 or lower, and preferably 7.2 or lower. If the pH exceeds 7.4, the measurement tends to be easily influenced by a non-pancreatic lipase. Besides, the pH is preferably 6.0 or higher. If the pH is lower than 6.0, there is a tendency that sufficient intensity of the lipase activity cannot be attained. The pH is more preferably 6.0 or higher and 7.2 or lower.

A higher fatty acid residue in the diglyceride may be any of higher fatty acids having 12 or more carbon atoms. Besides, one of such higher fatty acids may be singly used or a combination of different two of these may be used. For example, a saturated higher fatty acid such as lauric acid, myristic acid, palmitic acid, stearic acid or arachidic acid, and an unsaturated higher fatty acid such as palmitoleic acid, oleic acid, linoleic acid, linolenic acid or arachidonic acid are preferably used because a solution prepared by using such a diglyceride as a substrate has high clearness.

Examples of a diglyceride of preferable fatty acid include, but are not limited to, 1,2-dioleyl glycerol, 1-palmitoyl-2-oleyl glycerol, and a diglyceride derived from purified yolk lecithin or purified soybean lecithin.

A commercially available product can be used as the diglyceride substrate. Alternatively, the diglyceride substrate can be obtained by precedently preparing a phosphatide such as 1,2-dioleyl glyceryl choline, 1-palmitoyl-2-oleyl glyceryl choline, purified yolk lecithin or purified soybean lecithin, and allowing phospholipase C to act on such a phosphatide. Alternatively, a diglyceride obtained by converting a part of 1,2-diglyceride into 1,3-diglyceride through an alkali treatment performed in the presence of a non-ionic surface active agent (namely, a mixture of 1,2-diglyceride and 1,3-diglyceride) can be used as a substrate of the human pancreatic lipase reaction.

The concentration of the diglyceride optimum for the human pancreatic lipase reaction is, but not limited to, in a range of preferably 0.35 to 2.5 mmol/L, and more preferably 0.5 to 1.5 mmol/L.

In the contact step, a non-ionic surface active agent is preferably present together with the diglyceride. Specific examples of the non-ionic surface active agent include, but are not limited to, polyoxyethylene (POE) higher alcohol ether, POE secondary alcohol ethoxylate, POE alkyl phenyl ether, POE alkyl ether, POE fatty acid ester, and POE sorbitan fatty acid ester. The non-ionic surface active agent is preferably a POE alkyl phenyl ether-based non-ionic surface active agent or a POE alkyl ether-based non-ionic surface active agent. A specific example of the POE alkyl phenyl ether-based non-ionic surface active agent includes POE nonyl phenyl ether. Besides, a specific example of the POE alkyl ether-based non-ionic surface active agent includes POE tridecyl ether.

The concentration of the non-ionic surface active agent to be employed is not especially limited, but it is used preferably in a concentration range at which the activity of a pancreas-derived lipase is suitably expressed and is not inhibited, and specifically, in a range, in terms of a molar ratio, of preferably 1.1 to 2.5 times, and more preferably 1.2 to 2.0 times as high as that of the diglyceride substrate. If the concentration of the non-ionic surface active agent exceeds 2.5 times as high as that of the diglyceride substrate in terms of a molar ratio, there is a tendency that the activity of the human pancreatic lipase is lowered and that the activity against a non-pancreatic lipase is increased (see, for example, Patent Literature 3).

The diglyceride substrate and the non-ionic surface active agent may be prepared as a diglyceride solution, that is, a mixture of these. The diglyceride solution can be obtained, for example, by adding a buffer solution containing the non-ionic surface active agent to the diglyceride, followed by stirring at 35° C. to 46° C., preferably at 37° C. to 44° C., for 1 to 7 hours, preferably 1.5 to 4 hours, or followed by performing an ultrasonic treatment at the above-described temperature for about 30 minutes. The method for obtaining the diglyceride solution is, however, not limited to this method. The buffer solution for dissolving the diglyceride may be appropriately selected from buffer solutions having buffering capacity in a pH range of 5 to 9.5.

A specific example of the colipase includes, but is not limited to, a pig pancreas-derived colipase. It is known that the concentration of the colipase is generally in a relationship corresponding to a saturation curve with the lipase enzyme activity and that the lipase activity becomes constant at a given concentration or higher. Accordingly, the proper concentration of the colipase in the measurement of the human pancreatic lipase activity can be easily determined experimentally. For example, if a colipase manufactured by Asahi Kasei Pharma Corporation is used, the concentration of the colipase is, but is not limited to, for example, 8 to 250 U/L, preferably 10 to 150 U/L, and further preferably 10 to 120 U/L.

In the contact step, a buffer solution is preferably used for keeping the pH at 7.4 or lower. This, however, does not limit the embodiment, but an acid such as hydrochloric acid or a base such as sodium hydroxide can be used for adjusting the pH. If a buffer solution is used, a buffer solution having buffering capacity at pH 7.4 or lower, for example, a Good's buffer such as TES, HEPES, TAPSO, POPSO, Tricine, Bicine or BES buffer can be used.

In the measurement method for human pancreatic lipase activity in a sample according to the present embodiment, procedures such as the order of mixing substances are not especially limited, but for example, from the practical viewpoint, the substances may be divided into two constituent reagents to be combined to cause a reaction. In this case, there is no need that the two reagents have the same pH as long as the pH at the time of the lipase activity measurement, namely, at the time of mixing the two reagents, is 7.4 or lower. The concentration of the buffer solution is not especially limited but is preferably in a range of 10 mmol/L or more to 250 mmol/L.

Besides, in this case, for example, 1) the diglyceride may be contained in one reagent with the bile salt contained in the other reagent, or 2) the diglyceride may be contained in one reagent with the colipase contained in the other reagent. In the case 1), the colipase may be added to either of or both of the reagents. In the case 2), the bile acid may be contained in either of or both of the reagents.

As a method employed in the detection step, for example, the colorimetric method or another method can be employed, and a product produced through the human pancreatic lipase reaction is appropriately measured by combining known reaction systems. For example, as the colorimetric method, if a monoglyceride produced from a diglyceride substrate is to be converted by using a monoglyceride lipase into fatty acid and glycerol, the released glycerol is detected by combining hydrogen peroxide ultimately produced by using glycerol kinase, glycero-3-phosphate oxidase or peroxidase with a hydrogen donor in the presence of a coupler such as 4-aminoantipyrine, so as to spectroscopically detect the thus colored dye. Alternatively, as a method different from the colorimetric method, for example, an ultraviolet (UV) method in which the released glycerol is combined with glycerol kinase, ADP-hexokinase or glucose-6-phosphate dehydrogenase to detect absorbance change based on reduced NAD (P) at 340 nm can be employed. Accordingly, the method employed in the detection step may be appropriately selected from such colorimetric method and other methods.

As the monoglyceride lipase used in the colorimetric method, the origin is not especially limited as long as it is an enzyme not acting on the diglyceride but specifically acting on the monoglyceride, and from the viewpoint of stable supply, a microorganism-derived enzyme is preferably used, and a *Bacillus*-derived enzyme is more preferably used. The lower limit value of its concentration when used as a coupled enzyme in the lipase reaction is preferably 0.5 U/ml or more, and the upper limit value is preferably 5 U/ml or less, which does not limit the present embodiment.

The origin of the glycerokinase is not especially limited, but an enzyme excellent in stability is preferably used, and a *Flavobacterium*-derived enzyme is more preferably used. The origin of the glycero-3-phosphate oxidase is not especially limited, but from the viewpoint of the stable supply, a microorganism-derived enzyme is preferably used, and a lactic bacteria-derived enzyme is more preferably used.

The hydrogen peroxide produced through the reaction of the glycero-3-phosphate oxidase produces a dye through oxidative condensation with peroxidase, a chromogen of a Trinder's reagent and a coupler. The origin of the peroxidase is not especially limited, but an enzyme derived from a horseradish already stably supplied is preferably used. Besides, as the hydrogen donor, a phenol derivative, an aniline derivative, a toluidine derivative or the like is preferred. Specific examples of the hydrogen donor include N,N-dimethylaniline, N,N-diethylaniline, 2,4-dichlorophenol, N-ethyl-N-(2-hydroxy-3-sulfopropyl)-3,5-dimethoxyaniline (DAOS), N-ethyl-N-sulfopropyl-3,5-dimethylaniline (MAPS), N-ethyl-N-(2-hydroxy-3-sulfopropyl)-3,5-dimethylaniline (MAOS), N-ethyl-N-(2-hydroxy-3-sulfopropyl)-m-toluidine (TOOS), N-ethyl-N-sulfopropyl-m-anisidine (ADPS), N-ethyl-N-sulfopropylaniline (ALPS), N-ethyl-N-sulfopropyl-3,5-dimethoxyaniline (DAPS), N-sulfopropyl-3,5-dimethoxyaniline (HDAPS), N-ethyl-N-sulfopropyl-m-toluidine (TOPS), N-ethyl-N-(2-hydroxy-3-sulfopropyl)-m-anisidine (ADOS), N-ethyl-N-(2-hydroxy-3-sulfopropyl) aniline (ALOS), N-(2-hydroxy-3-sulfopropyl)-3,5-dimethoxyaniline (HDAOS), N-sulfopropyl-aniline (HALPS), and N,N-bis(4-sulfobutyl)-3-methylaniline disodium (TODB) (all manufactured by Dojindo Laboratories).

The presence of the hydrogen peroxide can be verified by color development of a leuco-type reagent in the presence of peroxidase. Specific examples of such a reagent include o-dianisidine, o-tridine, 3,3'-diaminobenzidine, and 3,3',5, 5'-tetramethylbenzidine all manufactured by Dojindo Laboratories, and N-(carboxymethylaminocarbonyl)-4,4'-bis(dimethylamino)biphenylamine (DA64) and 10-(carboxymethylaminocarbonyl)-3,7-bis(dimethylamino) phenothiazine (DA67) both manufactured by Wako Pure Chemical Industries Ltd. Besides, the detection and the quantitative determination of the hydrogen peroxide can be performed not only by a spectroscopic method but also by, for example, a fluorescence method, a chemiluminescence method, an electrode method or the like.

Besides, ADP, that is, one of products of glycerol kinase used in the UV method, can be converted into glucose-6-phosphoric acid by ADP-dependent hexokinase (ADP-HK) in the presence of glucose. The origin of the ADP-HK is not especially limited, but from the viewpoint of the stable supply, a microorganism-derived enzyme is preferably used, and an enzyme derived from an extremely thermophilic *Pyrococcus* or *Thermococcus* bacterium excellent in storage stability is more preferably used. The glucose corresponding to the substrate of the ADP-HK can be used in a concentration of 2 to 50 mmol/L. The glucose-6-phosphoric acid corresponding to the product of the ADP-HK can be converted into reduced NAD or NADP by glycose-6-phosphate dehydrogenase in the presence of oxidized NAD or NADP. The origin of the glucose-6-phosphate dehydrogenase is not especially limited, but from the viewpoint of the stable supply, a microorganism-derived enzyme is preferably used. In particular, a *Leuconostoc*-derived enzyme is preferred.

For example, there may present a free glycerol in a biological component such as serum used as a sample. Therefore, no matter which of the colorimetric method and the UV method is employed, the free glycerol may cause a positive error in the measurement of the pancreatic lipase activity. Accordingly, it is preferable to eliminate a free glycerol present in a sample prior to the pancreatic lipase reaction.

If the colorimetric method is employed, a first colorimetric method reagent containing glycerokinase, glycero-3-phosphate oxidase, catalase or peroxidase, and a chromogen of a Trinder's reagent such as a phenol derivative, an aniline derivative or a toluidine derivative is prepared, a test liquid is added to the first colorimetric method reagent, and the resultant mixture is precedently heated, so that a free glycerol present in the test liquid can be eliminated, but the present embodiment is not limited to this method. Examples of the chromogen of a Trinder's reagent include, but are not limited to, the aforementioned chromogens. Besides, if the colorimetric method is employed, a second colorimetric method reagent containing a component of a coupler such as 4-aminoantipyrine or 3-methyl-2-benzothiazolinone hydrazone (MBTH) is prepared. Here, if catalase is used in the first colorimetric method reagent, a catalase inhibitor such as sodium nitride may be contained in the second colorimetric method reagent. At the same time as the first colorimetric method reagent and the second colorimetric method reagent are mixed with each other, hydrogen peroxide produced through a reaction of glycero-3-phosphate oxidase produces a dye through the oxidative condensation with the chromogen of a Trinder's reagent and the coupler, and therefore, the increasing rate of this dye can be spectroscopically measured.

If the UV method is employed, as a method for avoiding the influence of a free glycerol, a first UV method reagent containing glycerol kinase, ADP-hexokinase, glucose-6-phosphate dehydrogenase, glucose and NAD (P) is prepared, and a test liquid is added to the first UV method reagent so as to precedently convert the free glycerol into reduced NAD (P). Besides, when an oxidase acting on glycerol (glycerol oxidase) is added to the first UV method reagent to convert the free glycerol into aldehyde, the influence of the free glycerol can be avoided. In this case, however, glycerol kinase and/or ATP is added to a second UV method reagent so that a glycerol kinase reaction cannot occur in the first UV method reagent. As the glycerol oxidase, any of known glycerol oxidases, such as *Aspergillus*-derived, *Neurospora*-derived and *Penicillium*-derived glycerol oxidases, can be used, which does not limit the present embodiment (see, for example, Non Patent Literature 5).

If the absorbance change based on the reduced NAD (P) is measured by the UV method, turbidity is caused in mixing the reagent with a given type of samples, and the turbidity may influence the absorbance at the measurement wavelength of 340 nm in some cases. In such a case, the influence of the turbidity can be avoided by measuring a sample blank for each sample. In order to increase the measurement sensitivity, a detection system having a high molecular extinction coefficient is preferably used. In this case, sensitivity higher than that attained in detection using the reduced NAD (P) can be attained by selectively using a dye having a higher molecular extinction coefficient than that of the reduced NAD (P), such as thio-NAD (P).

The method employed in the detection step is not limited to the colorimetric method and the UV method, but any other existing methods or a combination of these methods may be employed, and from the viewpoint of measurement complication, measurement accuracy and measurement sensitivity, a practical method may be appropriately selected.

The present invention will now be specifically described with reference to examples, and it is noted that the present invention is not limited to the following examples.

(Example 1) Type of Bile Acid and Active pH of Pancreatic Lipase

Preparation of Diglyceride Original Liquid

After weighing 1,2-dioleoyl glycerol (DODG) (manufactured by Nippon Fine Chemical Co., Ltd.) to attain a concentration of 9.32 mmol/L when dissolved, 1% polyoxyethylene (10) nonyl phenyl ether (NPE) (manufactured by Wako Pure Chemical Industries Ltd.) containing 1.66 mmol/L of MES (manufactured by Dojindo Laboratories) was added thereto to be dissolved therein by stirring at 37°

C. for 2 hours, and the resultant was allowed to stand still in ice for 2 hours or more. The thus obtained solution was used as a substrate original liquid.

Preparation of Reaction Solutions

The above-described diglyceride original liquid was used for preparing a "substrate stock solution" having the following composition:

| | |
|---|---|
| 5.6 mol/L | 1,2-dioleoyl glycerol |
| 0.6% | NPE |
| 1 mmol/L | MES |
| 3.2 mmol/L | magnesium sulfate |

A "first reaction solution (R-1)" having the following composition was prepared:

| | |
|---|---|
| 75 mmol/L | buffer solution |
| 4 mmol/L | calcium chloride |
| a concentration described later | bile salt |
| 3 mmol/L | ATP |
| 3 mmol/L | NADP |
| 3000 U/L | glycerol kinase (GKZ) (manufactured by Asahi Kasei Pharma Corporation) |
| 7500 U/L | ADP-dependent hexokinase (ADP-HKPII) (manufactured by Asahi Kasei Pharma Corporation) |
| 3000 U/L | glucose-6-phosphate dehydrogenase (G6PD) (manufactured by Toyobo Co., Ltd.) |
| 3 mmol/L | glucose |
| 3 mmol/L | magnesium chloride |

A "second reaction solution (R-2)" having the following composition was prepared:

| | |
|---|---|
| 50 mmol/L | buffer solution |
| 10,000 U/L | monoglyceride lipase (MGLPII) (manufactured by Asahi Kasei Pharma Corporation) |
| 60,000 U/L | colipase (CoLP) (manufactured by Asahi Kasei Pharma Corporation) |

A "second reaction solution (R-2) for sample blank" having the following composition was prepared:

| | |
|---|---|
| 50 mmol/L | buffer solution |
| 60,000 U/L | colipase (CoLP) (manufactured by Asahi Kasei Pharma Corporation) |

Measurement Operation

A mixture of the substrate stock solution and the R-1 in a proportion of 1:2 was used as a first reagent. The R-2 was directly used as a second reagent. As a sample, pooled serum or a control sample (a control containing a pancreatic lipase) was used. A proportion in amount among the sample, the first reagent and the second reagent was set as sample:first reagent:second reagent of 0.01 ml:0.18 ml:0.06 ml. The sample was added to the first reagent, the resultant mixture was heated at 37° C. for 5 minutes, the second reagent was added thereto, and a change rate of an absorbance at 340 nm based on reduced NADP was obtained at 37° C. from 3 minutes after the addition of the second reagent to 4 minutes after the addition, and then, the lipase activity was calculated by using a molecular extinction coefficient of 6300 L/mol·cm of the reduced NADP. Besides, as a sample blank, saline was used instead of a sample, an absorbance was measured by using the reagent for sample blank obtained by removing MGLPII from the second reagent, and a difference between the thus measured two values was defined as an enzyme activity value. For the measurement, Hitachi automatic analyzer Model H7170 or H7080 was used.

Measurement

As a conjugated bile acid to be added to the R-1, sodium taurodeoxycholate (NaTDCA), sodium glycodeoxycholate (NaGDCA), sodium glycochenodeoxycholate (NaGCDCA), sodium taurochenodeoxycholate (NaTCDCA), sodium glycocholate (NaGCA), sodium taurocholate (NaTCA) and sodium tauroursodeoxycholate (NaTUDCA) all in a concentration of 40 mmol/L were selected, the R-1 was adjusted, by using BES (manufactured by Dojindo Laboratories) respectively to pH 6.8, 7.0, 7.2, 7.4, 7.8, and 8.0, and the human pancreatic lipase activity was measured by using these. The pH of the R-2 was adjusted to be equal to that of the R-1.

The measurement results of the human pancreatic lipase activity of the pooled serum are shown in FIG. 1. In using NaTDCA, the pH for giving a maximum value of the activity was about 7, in using NaGDCA, the pH for giving a maximum value of the activity was about 7.2 to 7.4, and in using NaGCDCA or NaTCDCA, the pH for giving a maximum value of the activity was lower than 6.8. Therefore, in either case, the pH for giving a maximum value of the human pancreatic lipase activity (i.e., the apparent optimum pH) was lower than 7.5. In using NaGCA, NaTCA and NaTUDCA, the degree of the activation was extremely low and below detection limit.

As Comparative Examples, non-conjugated bile acids of sodium cholate (NaCA), sodium deoxycholate (NaDCA), sodium chenodeoxycholate (NaCDCA) and sodium ursodeoxycholate (NaUDCA) were used for performing similar operations at various pHs. It is noted that the concentration of each non-conjugated bile acid was set to be 24 mmol/L in the R-1. Besides, BES was used for adjusting pH to 7.2, 7.6, 7.8 and 8.0, and Bicine was used for adjusting pH to 8.2 and 8.5.

Figure 2:
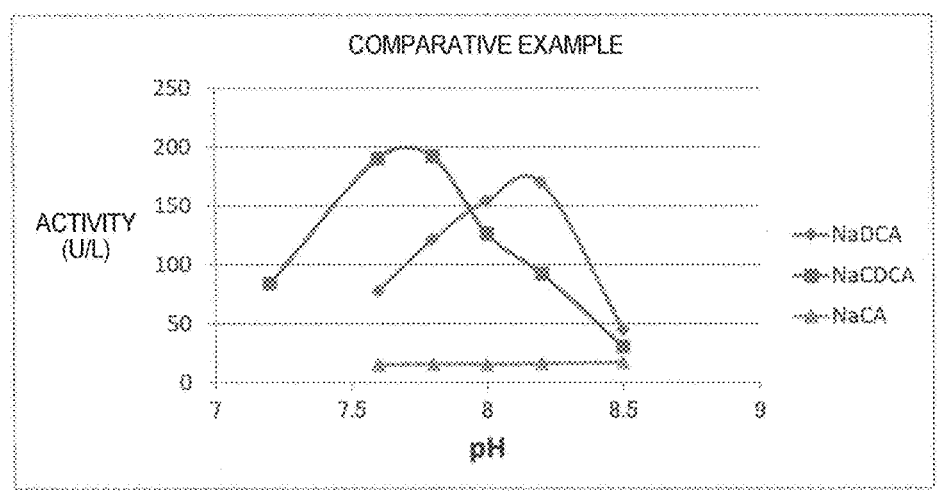
FIG. 2 is a graph illustrating the pH dependence of the human pancreatic lipase activity in the presence of a sodium salt of a non-conjugated bile acid according to a Comparative Example in Example 1.

The measurement results of the human pancreatic lipase activity in a pooled serum according to the Comparative Examples are shown in FIG. 2. In using NaDCA, the pH for giving a maximum value of the activity (i.e., the apparent optimum pH) was about 8.2, and in using NaCDCA, the pH for giving a maximum value of the activity (i.e., the apparent optimum pH) was about 7.7. In using NaUDCA, the measurement could not be performed because turbidity was caused in the R-1 reaction solution. Besides, in using NaCA, merely a slight signal could be obtained as compared with the case where NaDCA was used.

(Example 2) Effect of Combining NaTUDCA, NaGCA and NaTCA

Preparation of Reaction Solutions

A "substrate stock solution" having the following composition was prepared:

| | |
|---|---|
| 5.6 mol/L | 1,2-dioleoyl glycerol |
| 0.6% | NPE |
| 1 mmol/L | MES |
| 3.2 mmol/L | magnesium sulfate |

A "first reaction solution (R-1)" having the following composition was prepared:

| | |
|---|---|
| 75 mmol/L | buffer solution |
| 4 mmol/L | calcium chloride |
| a concentration described later | bile salt |
| 4 mmol/L | ATP |
| 3 mmol/L | NADP |
| 3000 U/L | GKZ |
| 8000 U/L | ADP-HKPII |
| 3000 U/L | G6PD |
| 3 mmol/L | glucose |
| 3 mmol/L | magnesium chloride |

A "second reaction solution (R-2)" having the following composition was prepared:

| | |
|---|---|
| 50 mmol/L | buffer solution |
| 10,000 U/L | MGLPII |
| 60,000 U/L | CoLP |

Measurement Operation

Similarly to Example 1, a mixture of the substrate stock solution and the R-1 in a proportion of 1:2 was used as a first reagent. Except for this, the measurement was performed in the same manner as in Example 1.

Measurement

Each of NaTCA, NaTCA and NaTUDCA, that is, the conjugated bile salt that did not singly sufficiently activate the human pancreatic lipase in Example 1, was combined with a non-conjugated bile acid, NaDCA, to examine the pH for giving a maximum value of the human pancreatic lipase activity (the apparent optimum pH). Besides, NaTCA was also combined with a conjugated bile acid, NaTDCA, to examine the pH for giving a maximum value of the human pancreatic lipase activity (the apparent optimum pH). It is noted that a BES buffer was used for adjusting pH to 6.9, 7.2 and 7.7, and a Bicine buffer was used for adjusting pH to 7.95 and 8.2. In each of the combinations of NaGCA/NaDCA, NaTCA/NaDCA, NaTUDCA/NaDCA and NaTCA/NaTDCA, the concentration of each bile acid was set to 20 mmol/L in the R-1. With respect to the combination of NaTCA and NaTDCA, a concentration of 40 mmol/L of NaTDCA was used as a control.

Figure 3:
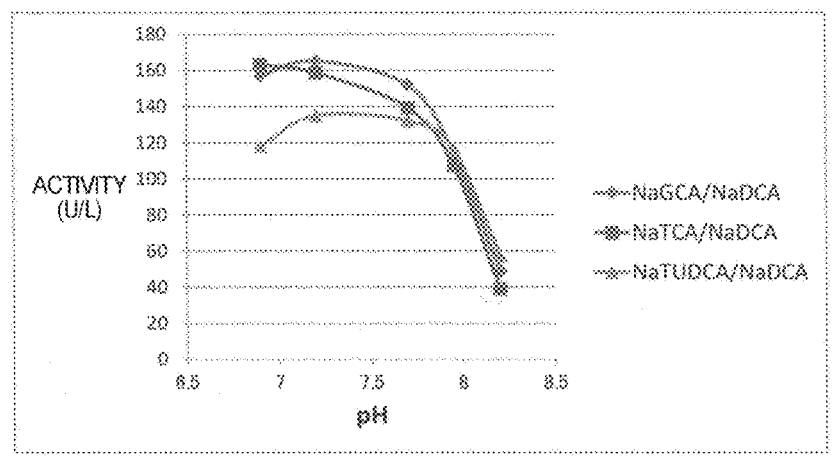
FIG. 3 is a graph illustrating the pH dependence of the human pancreatic lipase activity in the presence of sodium salts of a b-1-type bile acid and a b-2-type bile acid according to Example 2.
Figure 4:
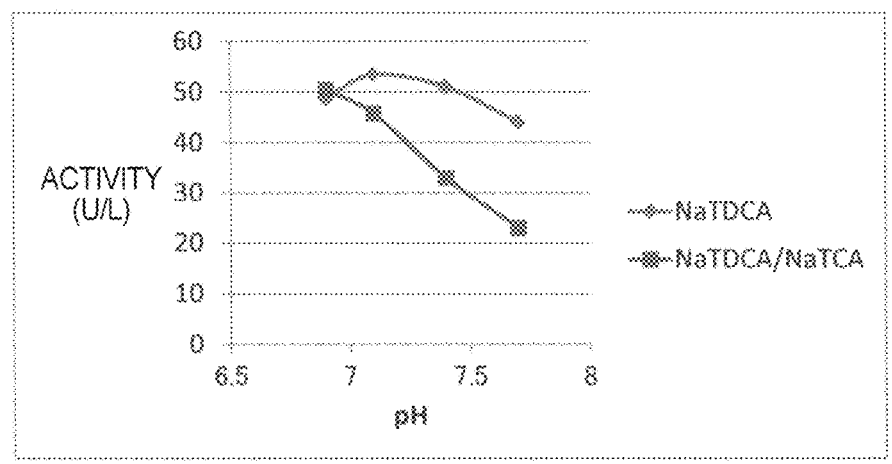
FIG. 4 is a graph illustrating the pH dependence of the human pancreatic lipase activity in the presence of an a-1-type bile acid according to Example 2 with a b-1-type bile acid added.

FIG. 3 shows the results obtained by the combinations of NaGCA/NaDCA, NaTCA/NaDCA and NaTUDCA/NaDCA. Although the optimum pH obtained by using NaDCA alone in the Comparative Example in Example 1 was about 8.2, the pH for giving a maximum value of the human pancreatic lipase activity (the apparent optimum pH) was changed to about 7.2 in combination with NaGCA, about 6.9 in combination with NaTCA, and about 7.4 in combination with NaTUDCA. Besides, as illustrated in FIG. 4, similarly to the results of Example 1, although the optimum pH obtained by using NaTDCA was about 7.1, the pH for giving a maximum value of the human pancreatic lipase activity (the apparent optimum pH) was further moved to the acid side when it was used in combination with TCA. The following was understood from these results: Although NaGCA, NaTCA and NaTUDCA were insufficient for the activation of the human pancreatic lipase when singly used, if they are used in combination with a specific bile acid, the activation of the human pancreatic lipase can be sufficiently attained, and an effect of moving, to the acid side, the pH for giving a maximum value of the human pancreatic lipase activity can be exhibited.

(Example 3) Mixing Proportion Between NaTDCA and NaDCA, and Active pH

The compositions of the reagents and the measurement operation were the same as those of Example 2. With respect to the conjugated bile acid NaTDCA singly attaining the optimum pH of the human pancreatic lipase of about 7 and the non-conjugated bile acid NaDCA singly attaining the optimum pH of the human pancreatic lipase of about 8.2, it was examined, by using a pooled serum, how the pH for giving a maximum value of the human pancreatic lipase activity was changed when the mixing proportion (molar ratio) therebetween was changed. The BES buffer was used for adjusting pH to 6.9, 7.1, 7.55 and 7.75, and the Bicine buffer was used for adjusting pH to 7.95, 8.15 and 8.4.

Figure 5:
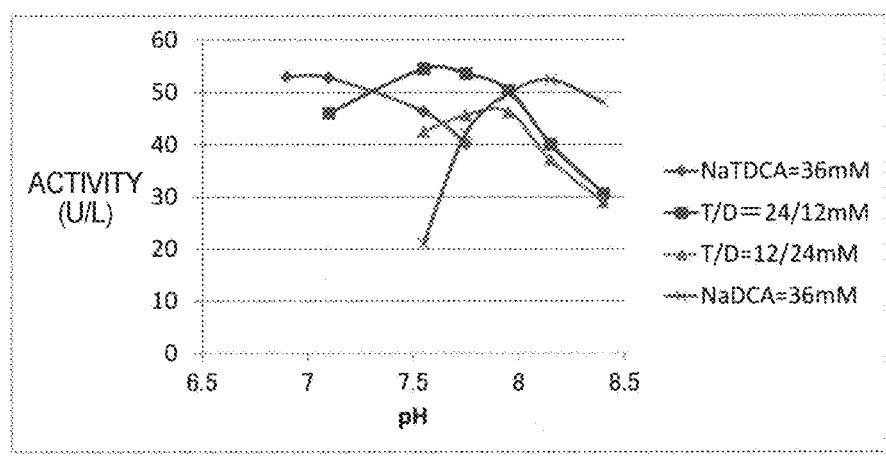
FIG. 5 is a graph illustrating the pH dependence of the human pancreatic lipase activity attained in varying a mixing proportion (molar ratio) between sodium taurodeoxycholate (NaTDCA) and sodium deoxycholate (NaDCA) according to Example 3.
Figure 6:
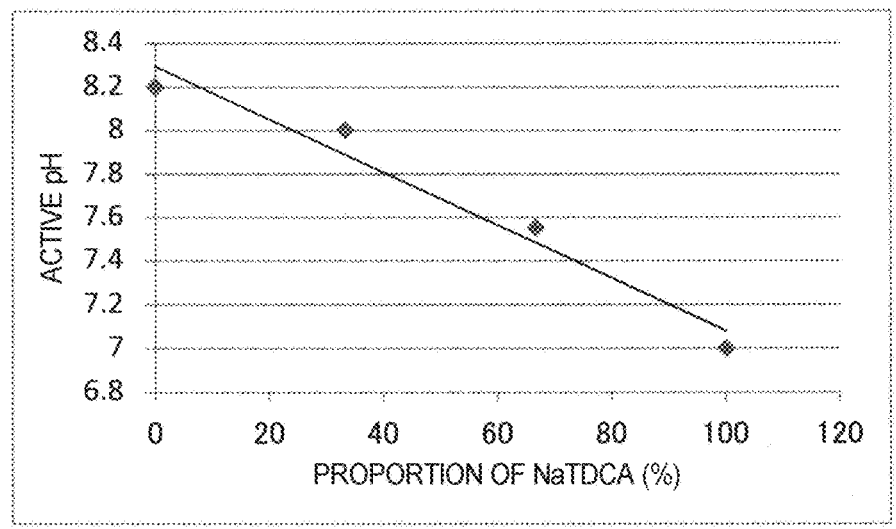
FIG. 6 is a graph illustrating the relationship between the mixing proportion between NaTDCA and NaDCA according to Example 3 and an active pH of human pancreatic lipase.

As illustrated in FIG. 5, if the content of NaTDCA was 67%, the pH for giving a maximum value of the human pancreatic lipase activity was about 7.55, and if the content was 33%, the pH for giving a maximum value of the human pancreatic lipase activity was about 8. Besides, on the basis of these results, when a proportion of NaTDCA to all added bile acids and the pH for giving a maximum value of the human pancreatic lipase activity are respectively plotted on the abscissa and ordinate, they are substantially linearly plotted as illustrated in FIG. 6. Thus, it was revealed that the pH for giving a maximum value of the human pancreatic lipase activity can be predicted based on a mixing proportion of bile acids.

(Example 4) Mixing Proportion of NaGCA and NaDCA, and Active pH

The compositions of the reagents and the measurement operation were the same as those of Example 2. NaGCA was selected from the conjugated bile acids that did not singly sufficiently activate the human pancreatic lipase, and a non-conjugated bile acid of NaDCA, which singly attains the optimum pH of the human pancreatic lipase of about 8.2, was used to change the mixing proportion (molar ratio) NaDCA/NaGCA, in terms of a final concentration, to be 24 mmol/L/0, 16 mmol/L/8 mmol/L, 12 mmol/L/12 mmol/L, 8 mmol/L/16 mmol/L, and 6 mmol/L/18 mmol/L, and it was examined, by using a control sample (a control containing a pancreatic lipase), how the pH for giving a maximum value of the human pancreatic lipase activity was changed. The BES buffer was used for adjusting pH to 7.2 and 7.6, and the Bicine buffer was used for adjusting pH to 8.0 and 8.5.

Figure 7:
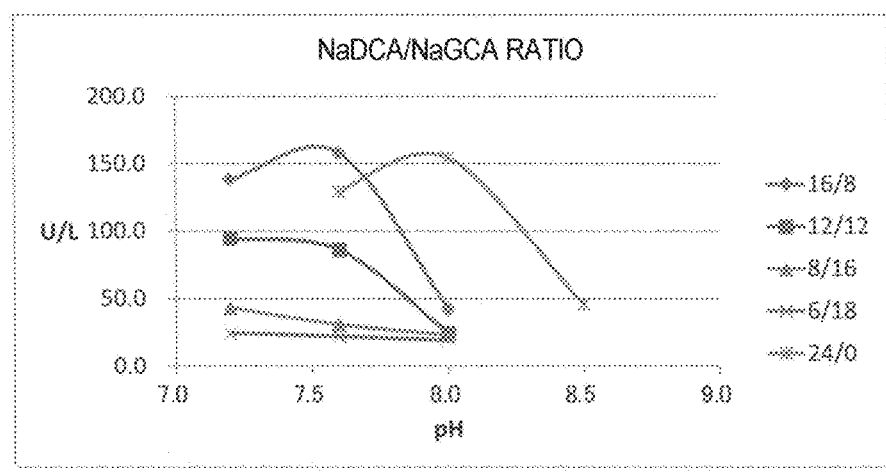
FIG. 7 is a graph illustrating the pH dependence of the pancreatic lipase activity attained in varying a mixing proportion (molar ratio) between sodium glycocholate (NaGCA) and sodium deoxycholate (NaDCA) according to Example 4.
Figure 8:
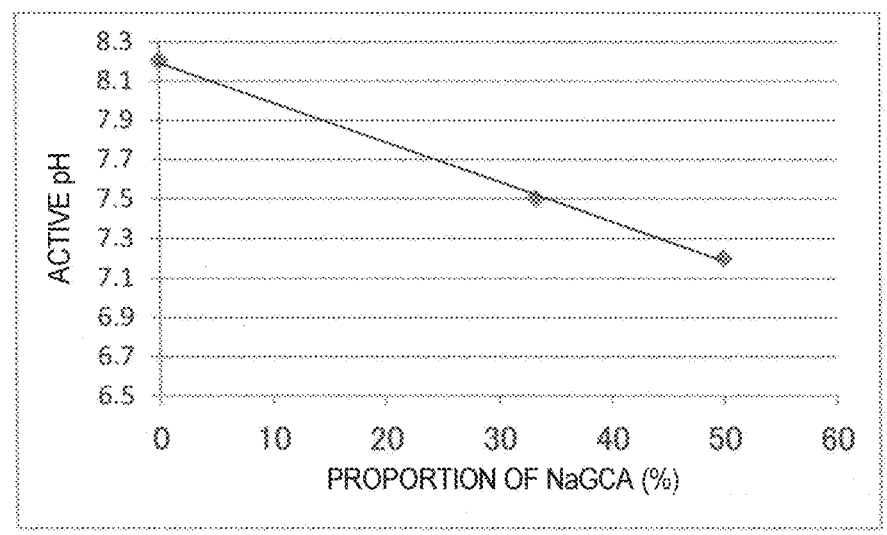
FIG. 8 is a graph illustrating the relationship between the mixing proportion between NaGCA and NaDCA according to Example 4 and the active pH of the human pancreatic lipase.

The results are shown in FIG. 7. As the amount of NaGCA was increased, the pH for giving a maximum value of the human pancreatic lipase activity was moved to the acid side, and the sensitivity was simultaneously lowered. On the basis of these results, when a proportion of NaGCA to all the added bile acids and the pH for giving a maximum value of the human pancreatic lipase activity are plotted respectively on the abscissa and ordinate as illustrated in FIG. 8, they are plotted substantially linearly, and thus, it was revealed that the pH for giving a maximum value of the human pancreatic lipase activity can be predicted based on a mixing ratio between bile acids.

(Example 5) Single Use of Conjugated Bile Acid and Reduction of Influence of Non-Pancreatic Lipase The compositions of the reagents and the measurement operation were the same as those of Example 2.

Measurement

A commercially available reagent for a resorufin colorimetric method, "Liquitech Lipase Color II" manufactured by Roche Diagnostics using 1,2-O-dilauryl-rac-glycerol-3-glutaric acid-(6-methylresorufin)ester (DGGR), which is regarded not to be influenced by a non-pancreatic lipase, such as a lipoprotein lipase or a hepatic lipase, appearing in blood due to administration of heparin, was used for verifying the effect of the present example. "Liquitech Lipase Color II" was used in accordance with the package insert, and a special calibrator was used for calculating the enzyme activity. As a comparative example, a regent in which NaDCA (in a concentration of 40 mmol/L in the R-1) was used as the bile acid and the reaction solution had pH 8.15 (the Bicine buffer) was prepared, and as reagent compositions of the present example, (1) a reagent in which MOPS (pH 7.0) was used as the buffer solution of the R-1 and R-2 and NaTDCA was used as the bile acid, (2) a reagent in which MOPS (pH 7.0) was used as the buffer solution of the R-1 and R-2 and NaGDCA was used as the bile acid, and (3) a reagent in which BES (pH 7.0) was used as the buffer solution of the R-1 and R-2 and NaGCDCA was used as the bile acid were respectively prepared. The concentration of each bile acid used in the present example was set to be the same as that in the comparative example.

Figure 9:
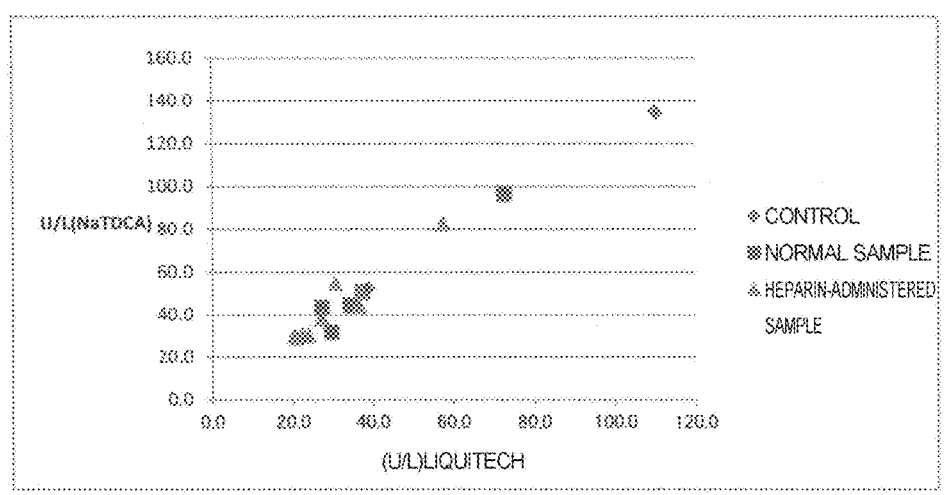
FIG. 9 is a graph illustrating the correlation between a measured value of human pancreatic lipase activity according to Example 5 and a measured value of human pancreatic lipase activity obtained by "Liquitech Lipase Color II".

As samples, a control, non-heparin-administered samples (normal samples), and heparin-administered samples were used. The results are shown in Table 1. First, in using NaTDCA, measured values obtained in the control and the normal samples were, as compared with those obtained by the comparative example, 77 to 112%, and those obtained in the heparin-administered samples were 28 to 52%, in using NaGDCA, the measured values were respectively 76 to 121% and 32 to 55%, and in using NaGCDCA, the measured values were respectively 70 to 98% and 26 to 48%. Thus, in using either bile acid, the activity in the heparin-administered samples was remarkably low as compared with that obtained by using the comparative example, which reveals that the influence of a non-pancreatic lipase, mainly of a lipoprotein lipase and a hepatic lipase, was reduced. FIG. 9 illustrates the correlation between the results obtained by Liquitech Lipase Color II and the results obtained by the present example using NaTDCA as the bile acid. The results of the heparin-administered samples are distributed on substantially the same line as those of the non-heparin-administered samples (normal samples), and thus, the effect of the present example was verified.

TABLE 1

| | Liquitech U/L | (1) Comparative example NaDCA Bicine (pH 8.15) U/L | (2) NaTDCA MOPS (7.0) U/L | (3) NaGDCA MOPS (7.0) U/L | (4) NaGCDCA BES (7.0) U/L | (2)/(1) NaTDCA % | (3)/(1) NaGDCA % | (4)/(1) NaGCDCA % |
|---|---|---|---|---|---|---|---|---|
| PRECIPATH ™ | 110.1 | 128.0 | 134.6 | 124.6 | 109.9 | 105.2 | 97.4 | 85.9 |
| PRECINORM ™ | 38.8 | 51.0 | 52.1 | 52.2 | 42.3 | 102.1 | 102.4 | 82.9 |
| Normal sample 1 | 27.1 | 39.1 | 43.4 | 47.1 | 38.1 | 111.1 | 120.6 | 97.5 |
| Normal sample 2 | 72.5 | 95.0 | 96.4 | 91.5 | 75.6 | 101.4 | 96.3 | 79.5 |
| Normal sample 3 | 37.4 | 46.6 | 50.7 | 49.7 | 41.2 | 108.7 | 106.5 | 88.4 |
| Normal sample 4 | 34.4 | 43.5 | 44.5 | 32.9 | 31.7 | 102.3 | 75.8 | 73.0 |
| Normal sample 5 | 29.6 | 40.7 | 31.7 | 36.2 | 28.8 | 77.8 | 89.0 | 70.8 |
| Heparin 1 | 20.4 | 76.8 | 30.1 | 39.1 | 30.8 | 39.2 | 50.9 | 40.1 |
| Heparin 2 | 36.7 | 86.7 | 44.2 | 47.5 | 41.3 | 50.9 | 54.8 | 47.6 |
| Heparin 3 | 27.2 | 112.9 | 37.9 | 36.9 | 29.8 | 33.6 | 32.7 | 26.4 |
| Heparin 4 | 20.9 | 101.4 | 28.9 | 28.2 | 31.6 | 28.5 | 27.8 | 31.2 |
| Heparin 5 | 22.4 | 68.5 | 30.1 | 23.8 | 17.8 | 44.0 | 34.8 | 26.0 |
| Heparin 6 | 23.9 | 69.2 | 30.1 | 28.9 | 22.5 | 43.4 | 41.8 | 32.5 |
| Heparin 7 | 37.2 | 138.3 | 50.4 | 58.0 | 51.0 | 36.4 | 42.0 | 36.9 |
| Heparin 8 | 30.7 | 126.0 | 54.7 | 43.9 | 36.6 | 43.4 | 34.8 | 29.0 |
| Heparin 9 | 57.4 | 168.8 | 82.4 | 81.0 | 75.4 | 48.8 | 48.0 | 44.7 |

(Example 6) Combination of Bile Acids and Reduction of Influence of Non-Pancreatic Lipase The compositions of the reagents were the same as those of Example 2. As a comparative example, NaDCA (in a concentration of 40 mmol/L in the R-1) was used as the bile acid, and the reaction solution was adjusted to pH 8.15 (by the Bicine buffer) for measuring a heparin-administered sample. Besides, as conjugated bile acids of the present example, NaGCA, NaTCA and NaTCDCA, which could not singly show a sufficient activation effect, were used respectively in combination with a non-conjugated bile acid of NaDCA or NaCDCA, and NaGCDCA and NaTCDCA, which singly showed a sufficient activation, were used for measuring a heparin-administered sample (BES (pH 7.1), with the bile acid contained in a concentration of 40 mmol/L in the R-1 (whereas mixed in equal amounts in employing a combination)).

It is noted that CRM-001b containing a human pancreatic recombinant lipase dissolved not in distilled water but in a pooled serum was used as the calibrator to calculate the lipase activity. As a result, as shown in Table 2, activity values of heparin-administered samples were greatly reduced in the present example as compared with the comparative example. Accordingly, it was revealed that the influence of the non-pancreatic lipase can be reduced in the present example.

TABLE 2

|  | Comparative example | Present example | | | | | | | |
|---|---|---|---|---|---|---|---|---|---|
| Free bile salt |  | NaDCA | NaDCA | NaDCA | NaCDCA | NaCDCA | NaCDCA | — | — |
| Conjugated bile salt | — | NaGCA | NaTCA | NaTUDCA | NaGCA | NaTCA | NaTUDCA | NaGCDCA | NaTCDCA |
| pH | 8.15 | 7.1 | 7.1 | 7.1 | 7.1 | 7.1 | 7.1 | 7.1 | 7.1 |
| Heparin 1 (U/L) | 141.3 | 44.8 | 45.5 | 56.1 | 42.8 | 47.7 | 52.7 | 47.8 | 54.5 |
| Heparin 2 (U/L) | 58.5 | 18.6 | 23.4 | 29.6 | 18.5 | 34.6 | 36.1 | 25.9 | 31.7 |
| Heparin 3 (U/L) | 127.3 | 42.5 | 42.6 | 48.6 | 45.1 | 63.7 | 50.0 | 44.0 | 48.1 |

(Example 7) Quantitative Evaluation of Influence of Non-Pancreatic Lipase (pH Dependence): NaTDCA As a bile acid of the present example and a reference example, NaTDCA was selected, and the pH dependence with the pH of a reaction solution changed in a range of 6.2 to 7.6 was examined. It is noted that a case of pH 7.6 was used as the reference example. An MES buffer was used for adjusting pH to 6.2 and 6.4, and the BES buffer was used for adjusting the other pHs. As samples, (six) control samples (controls each containing a pancreatic lipase) and (nine) heparin-administered samples were used. As a comparative example, NaDCA (in a concentration of 40 mmol/L in the R-1) was used as the bile acid, and a reaction solution having pH 8.15 (the Bicine buffer) was used. Besides, "Liquitech Lipase Color II" manufactured by Roche Diagnostics was used for verifying the effect of the present example. "Liquitech Lipase Color II" was used in accordance with the package insert, and a special calibrator was used for calculating the enzyme activity. The results are shown in Table 3.

Next, the influence of the non-pancreatic lipase activity was obtained as follows on the assumption that the Liquitech reagent is not influenced by the non-pancreatic lipase. First, with respect to measured values of the enzyme activity obtained in samples other than the heparin-administered samples, a regression equation (an independent variable X: enzyme activity attained by Liquitech, a dependent variable Y: enzyme activity attained by the comparative example or the present example) was obtained. Next, with respect to each heparin-administered sample, the variable Y was calculated as a theoretical value by substituting the measured value of the enzyme activity obtained by the Liquitech for the variable X of the regression equation. Thereafter, with respect to each heparin-administered sample, the actually measured value of the enzyme activity obtained by the comparative example or the present example was divided by the theoretical value of the variable Y to calculate a relative percentage (%). The results are shown in Table 4. It is noted that the acceptable range of the influence was provisionally set as within ±20% in reference to the package insert of "Liquitech Lipase Color II" describing that the accuracy is within ±15% of known activity.

The results are shown in Table 4. As is obvious from Table 4, at pH 7.4 or lower, the actually measured values were smaller than 120.0% of the theoretical values on average, which is within the acceptable range, but at pH 7.6, the actually measured values were 212.1% on average, which is twice or more of the theoretical value. Accordingly, it was revealed that the influence of the non-pancreatic lipase can be reduced at pH 7.4 or lower.

TABLE 3

|  | Liquitech U/L | Comparative example pH 8.15 U/L | Reference example pH 7.6 U/L | Present example | | | | | | |
|---|---|---|---|---|---|---|---|---|---|---|
|  |  |  |  | pH 7.4 U/L | pH 7.2 U/L | pH 6.9 U/L | pH 6.6 U/L | pH 6.4 U/L | pH 6.2 U/L |
| Recombinant pancreatic lp-containing serum | 168.2 | 227.2 | 168.8 | 217.3 | 229.8 | 233.1 | 211.9 | 184.7 | 180.8 |
| PRECIPATH ™ | 110.1 | 153.3 | 110.7 | 152.7 | 159.2 | 157.3 | 140.3 | 109.5 | 110.7 |
| PRECINORM ™ | 38.8 | 56.7 | 52.0 | 57.1 | 59.5 | 67.1 | 52.6 | 50.0 | 46.8 |
| Pool 1 | 36.6 | 48.0 | 39.1 | 45.4 | 52.4 | 53.0 | 45.2 | 44.6 | 42.1 |
| Pool 2 | 22.3 | 24.2 | 18.3 | 27.0 | 28.2 | 28.0 | 23.6 | 24.8 | 22.8 |
| Seraclear | 26.0 | 26.8 | 20.2 | 31.4 | 33.8 | 31.7 | 28.6 | 25.4 | 23.7 |
| Heparin 21 | 33.6 | 42.9 | 34.7 | 44.5 | 47.6 | 48.6 | 40.9 | 37.9 | 35.9 |
| 22 | 37.2 | 47.9 | 38.3 | 49.2 | 52.6 | 53.6 | 45.5 | 41.7 | 39.7 |
| 23 | 57.4 | 76.0 | 58.6 | 75.8 | 80.5 | 81.7 | 71.4 | 63.0 | 61.0 |
| 24 | 42.1 | 54.7 | 43.2 | 55.7 | 59.4 | 60.4 | 51.8 | 46.9 | 44.9 |
| 25 | 35.6 | 45.7 | 36.7 | 47.1 | 50.4 | 51.4 | 43.5 | 40.0 | 38.0 |

TABLE 4

|  | Comparative example pH 8.15 % | Reference example pH 7.6 % | Present example | | | | | |
|---|---|---|---|---|---|---|---|---|
|  |  |  | pH 7.4 % | pH 7.2 % | pH 6.9 % | pH 6.6 % | pH 6.4 % | pH 6.2 % |
| Heparin 21 | 150.8 | 167.2 | 118.3 | 99.1 | 99.9 | 109.4 | 110.6 | 118.4 |
| 22 | 179.7 | 162.0 | 107.8 | 98.5 | 86.0 | 93.6 | 100.8 | 100.6 |
| 23 | 284.1 | 281.9 | 129.2 | 110.5 | 114.9 | 111.4 | 115.8 | 112.9 |

TABLE 4-continued

| | Comparative example | Reference example | Present example | | | | | |
|---|---|---|---|---|---|---|---|---|
| | pH 8.15 % | pH 7.6 % | pH 7.4 % | pH 7.2 % | pH 6.9 % | pH 6.6 % | pH 6.4 % | pH 6.2 % |
| 24 | 259.1 | 215.2 | 113.2 | 96.0 | 84.4 | 83.0 | 91.7 | 95.4 |
| 25 | 273.6 | 234.4 | 127.4 | 100.2 | 89.5 | 91.7 | 94.7 | 93.1 |
| Average | 229.5 | 212.1 | 119.2 | 100.9 | 94.9 | 97.8 | 102.7 | 104.1 |

(Example 8) Quantitative Evaluation of Effect of Reducing Influence of Non-Pancreatic Lipase (pH 7.1, 7.4, 7.6): NaGDCA/NaDCA In the present example, NaGDCA was selected as the conjugated bile acid and was combined with a non-conjugated bile acid, NaDCA, (mixed in equal amounts) to examine the behavior of a heparin-administered sample with the pH of a reaction solution changed to 7.1, 7.4 and 7.6. As the buffer solution, the BES buffer was used. As samples, (four) control samples (controls each containing a pancreatic lipase), (ten) normal samples and (nine) heparin-administered samples were used. As a comparative example, NaDCA (in a concentration of 30 mmol/L in the R-1) and NaTDCA (in a concentration of 10 mmol/L in the R-1) were used as the bile acid, and the reaction solution was adjusted to pH 7.95 (the Bicine buffer). Besides, "Liquitech Lipase Color II" manufactured by Roche Diagnostics was used for verifying the effect of the present example. "Liquitech Lipase Color II" was used in accordance with the package insert, and a special calibrator was used for calculating the enzyme activity. Thereafter, in the same manner as in Example 7, with respect to each heparin-administered sample, the actually measured value of the enzyme activity obtained by the comparative example or the present example was divided by the theoretical value to calculate a relative percentage (%). The influence of the non-pancreatic lipase activity and the acceptable range of the influence were the same as those in Example 7.

The results are shown in FIG. 10. As is obvious from FIG. 10, at pH 7.4 and 7.1, the actually measured values obtained in the heparin-administered samples were smaller than 120% of the theoretical values on average, which is within the acceptable range. On the contrary, as a reference example, at pH 7.6, the actually measured values were 194.7%, and in using the comparative example, the actually measured value was 198%, which is substantially twice of the theoretical value. Accordingly, it was revealed that if NaGDCA and NaDCA are used in combination and the pH is 7.4 or lower, the influence of the non-pancreatic lipase can be reduced.

(Example 9) Quantitative Evaluation of Effect of Reducing Influence of Non-Pancreatic Lipase by Combination of Bile Acids As a comparative example, NaDCA and NaTDCA (respectively in concentrations of 30 mmol/L and 10 mmol/L in the R-1) were used as the bile acids, and the reaction solution was adjusted to pH 7.95 by using the Bicine buffer to measure a heparin-administered sample. Besides, as the present example, NaTDCA, NaGDCA, NaGCA and NaTCA were used as the conjugated bile acids, NaDCA was used as the non-conjugated bile acid, and by using each of combinations of the non-conjugated and conjugated bile acids, combinations of conjugated bile acids, and combinations of two conjugated bile acids and the non-conjugated bile acid as shown in Table 6, a heparin-administered sample was measured (the BES (pH 6.9)). The bile acids were used in a total concentration in the R-1 of 40 mmol/L (each in 20 mmol/L in using two of them, and each in 13.3 mmol/L in using three of them). Besides, "Liquitech Lipase Color II" manufactured by Roche Diagnostics was used for verifying the effect of the present example. "Liquitech Lipase Color II" was used in accordance with the package insert, and a special calibrator was used for calculating the enzyme activity. In each of the comparative example and the present example, the lipase activity was calculated by using a molecular extinction coefficient of 6300 L/mol·cm of the reduced NADP. Thereafter, in the same manner as in Example 7, with respect to each heparin-administered sample, the actually measured value of the enzyme activity obtained by the comparative example or the present example was divided by the theoretical value to calculate a relative percentage (%). The influence of the non-pancreatic lipase activity and the acceptable range of the influence were calculated in the same manner as in Example 7.

As a result, as illustrated in FIG. 11, in using the comparative example, the actually measured values of the four heparin-administered samples were 204.5%, on average, of the theoretical value, but in using any combination of the present example, the actually measured value was within 100±15%, which is within the acceptable range, and thus, the influence of the non-pancreatic lipase was remarkably reduced.

(Example 10) Type of Surface Active Agent and Quantitative Evaluation of Effect of Reducing Influence of Non-Pancreatic Lipase In preparing the diglyceride original liquid described in Example 1, polyoxyethylene tridecyl ether (ADEKA TOL TN-100) (manufactured by ADEKA Corporation) was used as the surface active agent instead of the polyoxyethylene (10) nonyl phenyl ether (NPE) to be compared with that prepared by using NPE. It is noted that the concentration of the surface active agent was the same. As the conjugated bile acid of the present example, NaGDCA and NaTDCA (mixed in equal amounts) were selected, and a reaction solution of pH 7.2 and a reaction solution of pH 7.4 were prepared by using each of the surface active agents. Besides, as a comparative example, NaDCA (in 30 mmol/L in the R-1) and NaTDCA (in 10 mmol/L in the R-1) were used as the bile acids, and the reaction solution was adjusted to pH 7.95 by using the Bicine buffer. Furthermore, "Liquitech Lipase Color II" manufactured by Roche Diagnostics was used for examining the influence of the non-pancreatic lipase activity in the same manner as in Example 7.

The results obtained in heparin-administered samples alone are shown in FIG. 12. It is understood from the results that the actually measured values were within ±120% of the theoretical value in using either of the two surface active agents, and thus were not influenced by the non-pancreatic lipase, but the actually measured values of the comparative example using NPE were 150% and 210%, and thus the comparative example was influenced by the non-pancreatic lipase.

(Example 11) Comparison Between pH 7.5 or Higher and pH 7.5 or Lower

As a comparative example, NaDCA and NaTDCA (respectively in concentrations of 30 mmol/L and 10 mmol/L in the R-1) were used as the bile acids, and the reaction solution was adjusted to pH 7.95 by using the Bicine buffer. Besides, NaGCDCA (in 40 mmol/L in the R-1) was selected as the conjugated bile acid, and the effect was examined in two heparin-administered samples at pH 7.0 in the present example and at pH 7.95 in a reference example. First, calibration was carried out by using a recombinant pancreatic LP-containing serum, and a mixing proportion of a non-pancreatic lipase in the whole lipases was calculated on the assumption that a measured value of a heparin-administered sample obtained by the comparative example corresponds to the total activity of the human pancreatic lipase and the non-pancreatic lipase, and that a measured value of the present example corresponds to the activity of the human pancreatic lipase alone.

With respect to each of the present example and the reference example, a theoretical value Y of the human pancreatic lipase activity was calculated as follows, based on the measured value of the comparative example obtained by using a molecular extinction coefficient, in accordance with a correlation equation obtained without using a heparin-administered sample. It is noted that X represents a variable to be substituted for a measured value of the comparative example, a represents a slope, and b represents an intercept.

Pancreatic lipase activity (theoretical value)=(1−mixing proportion of non-pancreatic lipase)×(aX+b)

The results are shown in Table 5. First, the sensitivity was lowered to about 40% in the reference example employing pH 7.95 as compared with the present example employing pH 7.0. Besides, since the optimum pH of the non-pancreatic lipase contained in the heparin-administered sample is closer to the pH 7.95 than to the pH 7.0, the measured values of the enzyme activity were as high as 311.8% and 492.8% of the theoretical value of the pancreatic lipase. On the contrary, in the present example employing pH 7.0, the measured values were 98.4% and 98.5% of the theoretical value of the pancreatic lipase, and thus, it was revealed that the influence of the non-pancreatic lipase could be greatly avoided.

TABLE 5

| | | NaGCDCA | | Measured value/theoretical value NaGCDCA | |
|---|---|---|---|---|---|
| | Comparative example pH 7.95 U/L | Reference example 7.95 U/L | Present example 7.0 U/L | Reference example 7.95 % | Present example 7.0 % |
| Recombinant pancreatic lp-containing serum | 206.9 | 72.4 | 166.1 | 94.7 | 99.9 |
| PRECIPATH ™ | 134.5 | 57.3 | 109.9 | 111.6 | 100.9 |
| PRECINORM ™ | 50.8 | 24.0 | 42.3 | 107.6 | 99.3 |
| Pool 1 | 42.9 | 19.4 | 36.9 | 99.4 | 101.8 |
| Pool 2 | 21.6 | 15.4 | 17.5 | 126.2 | 89.8 |
| Seraclear LP | 22.4 | 7.5 | 17.5 | 60.4 | 87.0 |
| Heparin 31 | 99.2 | 60.7 | 40.7 | 311.8 | 98.4 |
| Heparin 32 | 104.8 | 77.0 | 32.7 | 492.8 | 98.5 |

Figure 13:
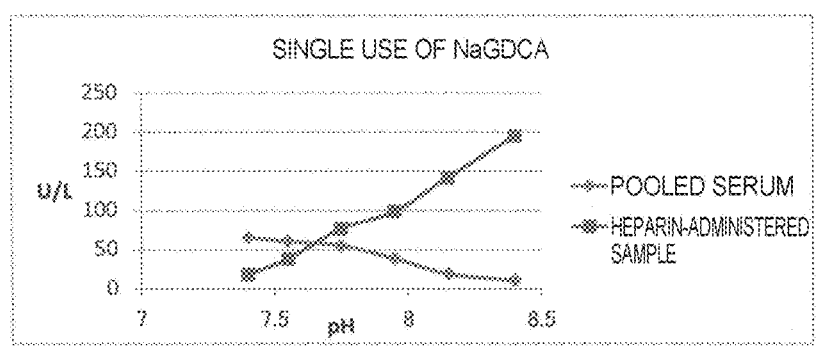
FIG. 13 is a graph illustrating the pH dependence of the human pancreatic lipase activity in a sample with or without administration of heparin in using NaGDCA according to Example 12.
Figure 14:
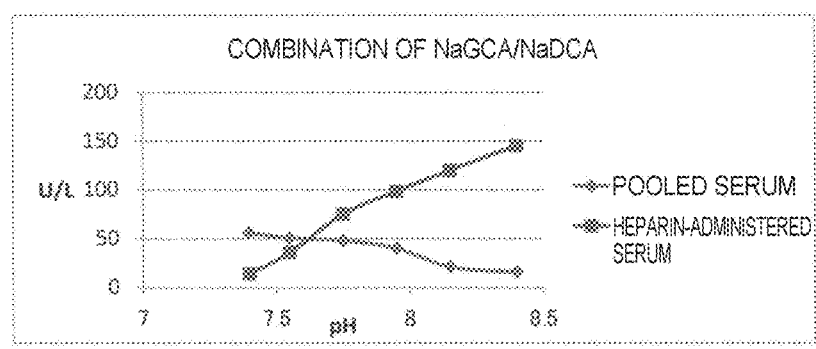
FIG. 14 is a graph illustrating the pH dependence of the lipase activity in a sample with or without administration of heparin in using NaGCA/NaDCA according to Example 12.
Figure 15:
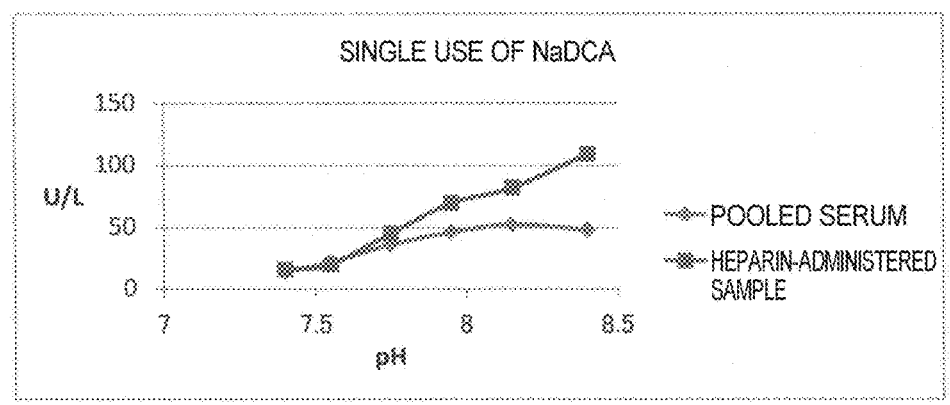
FIG. 15 is a graph illustrating the pH dependence of the human pancreatic lipase activity in a sample with or without administration of heparin in using NaDCA according to a comparative example in Example 12.

(Example 12) Comparison in Active pH Between Pancreatic Lipase and Non-Pancreatic Lipase With the pH of a reaction solution changed between 7.4 and 8.4, the lipase activity was measured in a human pooled serum and a heparin-administered serum. The BES buffer was used for adjusting pH to 7.4 and 7.55, and the Bicine buffer was used for adjusting the other pHs. In the present example, NaGDCA and NaGCA (which was combined with a non-conjugated bile acid of NaDCA (mixed in equal amounts to be in a total concentration of 40 mmol/L in the R-1)) were used as the conjugated bile acids. In a comparative example, NaDCA (Bicine, pH 8.15) was used. The results are shown in FIGS. 13, 14, and 15. While the pH for giving a maximum value of the human pancreatic lipase activity was about 8.2 in using the comparative example as illustrated in FIG. 15, the pH was about slightly lower than 7.4 in using the present example as illustrated in FIGS. 13 and 14. On the other hand, with respect to the heparin-administered sample, the activity was increased as the pH was increased in both the methods of the present example and the comparative example. These results reveal that the bile acids of the present example move the pH for giving a maximum value of the human pancreatic lipase activity to the acid side but does not change the pH for giving a maximum value of the non-pancreatic lipase activity. It is noted that different heparin-administered samples were used in this experiment.

(Example 13) Proportion Between Bile Acid and Substrate

Figure 16:
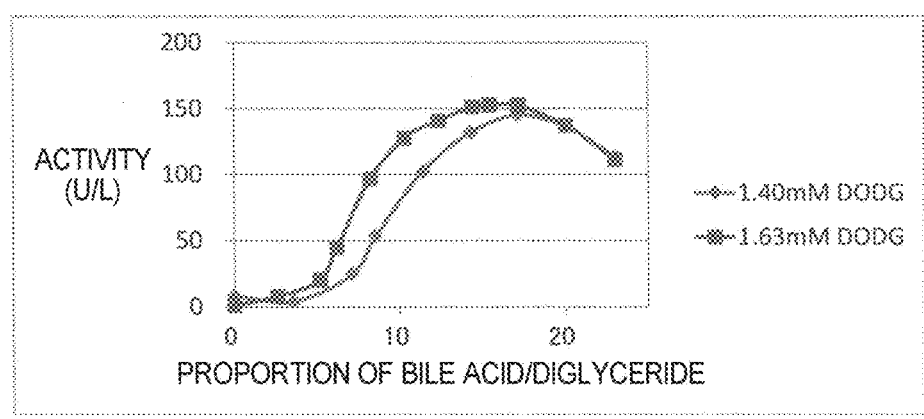
FIG. 16 is a relationship diagram between a ratio (molar ratio) between a bile acid and a diglyceride, and the human pancreatic lipase activity according to Example 13.

As a conjugated bile acid of the present example, NaTDCA was used for examining the influence of the concentration of the bile acid at pH 7.2 (the BES buffer). As a substrate diglyceride, 1,2-dioleoyl glycerol was used, and as a non-ionic surface active agent for dissolving the substrate, polyoxyethylene (10) nonyl phenyl ether (manufactured by Wako Pure Chemical Industries Ltd.) was used in a molar ratio of 1.74 to the diglyceride. Besides, the substrate concentration was set to a final concentration of 1.40 mmol/L and 1.63 mmol/L. The results are illustrated in FIG. 16. A proportion of the bile acid to the substrate for attaining the maximum lipase activity was about 17 when the substrate concentration was 1.40 mmol/L and was about 15 when the concentration was 1.63 mmol/L. Besides, if the proportion exceeded 20, the sensitivity tended to be lowered.

(Example 14) Verification of Effect by Using Commercially Available Color Method Reagent (Yolk Lecithin-Derived Diglyceride)

A commercially available reagent "Lipase Color Auto Test Wako" (manufactured by Wako Pure Chemical Industries Ltd.) using, as a substrate, 1,2-diglyceride prepared from yolk lecithin was used for verifying the effect. "Lipase Color Auto Test Wako" is composed of an enzyme substrate agent (freeze-dried vial), a dissolving liquid (a Good's buffer) and an activating solution (a Good's buffer pH 8.7, 4-aminoantipyrine, deoxycholic acid), and an enzyme substrate liquid obtained by dissolving the enzyme substrate agent in the dissolving liquid is used as a first reagent, and the activating solution is used as a second reagent.

In order to examine the effect, NaTDCA and NaGDCA in the form of a powder were added to the dissolving liquid into a concentration in the dissolving liquid of 12 mmol/L, and the resultant was adjusted to pH 7.0 by sodium hydroxide. Besides, a 150 mmol/L BES buffer (pH 7.0) containing 6 mmol/L of 4-aminoantipyrine was prepared to be used instead of the activating solution. Specifically, deoxycholic acid, that is, a bile acid, contained in the activating solution of the kit was excluded, and NaTDCA and NaGDCA were used instead. The thus obtained reaction solution was used for comparing a measurement result with a result obtained by the initial reagent not modified as described above. As samples, nine heparin-administered samples and five non-administered samples were used.

The results are shown in Table 6. In the non-heparin-administered samples, the present example in which the type of bile acid had been modified (i.e., the modified reagent) attained measured values of the activity of 94 to 108% of those attained by the commercially available reagent not modified. In the heparin-administered samples, the present example attained measured values of the activity of 40% to 62% of those attained by the commercially available reagent not modified. Accordingly, it was revealed that the present example can reduce the influence of the non-pancreatic lipase in a heparin-administered sample.

TABLE 6

|  | (1) Commercially available reagent U/L | (2) Modified reagent U/L | (2)/(1)(%) |
|---|---|---|---|
| Normal sample 43 | 38.0 | 37.0 | 97.4 |
| 44 | 70.4 | 70.4 | 100.0 |
| 45 | 43.5 | 41.4 | 95.2 |
| 46 | 36.9 | 39.6 | 107.5 |
| 47 | 34.7 | 32.6 | 94.0 |

TABLE 6-continued

|  | (1) Commercially available reagent U/L | (2) Modified reagent U/L | (2)/(1)(%) |
|---|---|---|---|
| Heparin 41 | 88.6 | 54.6 | 61.6 |
| Heparin 42 | 94.6 | 47.5 | 50.2 |
| Heparin 43 | 118.8 | 47.5 | 40.0 |
| Heparin 44 | 101.8 | 46.6 | 45.8 |
| Heparin 45 | 75.4 | 44.0 | 58.4 |
| Heparin 46 | 67.7 | 39.6 | 58.5 |
| Heparin 47 | 141.4 | 59.0 | 41.7 |
| Heparin 48 | 137.5 | 56.3 | 41.0 |
| Heparin 49 | 187.0 | 97.7 | 52.2 |

Example 15

As a comparative example, the pH of the R-1 and R-2 of Example 2 were changed to the Bicine buffer (pH 8.0), and 27 mmol/L of sodium deoxycholate (NaDCA) and 13 mmol/L of sodium taurodeoxycholate (NaTDCA) were used as the bile acid in the R-1 (in which the proportion of the NaTDCA in all bile acids was 33%). As a reagent composition of the present example, (1) the BES buffer (pH 7.2) was used as the buffer solutions of the R-1 and R-2, and 20 mmol/L of sodium taurodeoxycholate (NaTDCA) and 20 mmol/L of sodium glycodeoxycholate (NaGDCA) were added as the bile acids. Besides, as another reagent composition of the present example, (2) the BES buffer (pH 7.2) was used as the buffer solution and no bile acid was added in the R-1, the BES buffer (pH 7.2) was used as the buffer solution and 40 mmol/L of NaTDCA and 40 mmol/L of NaGDCA were added as the bile acids in the R-2. In this manner, the bile acids were added to the R-2 in the reagent (2). It is noted that the final concentration of the bile acids was the same as that in the reagent (1).

Measurement Operation

The same operation was performed as in Example 2 except for the calculation of the activity. In the present example and the comparative example, CRM-001b containing a human pancreatic recombinant lipase dissolved not in distilled water but in a pooled serum was used as the calibrator to calculate the lipase activity.

Samples

PRECIPATH™, PRECINORM™, ten non-heparin-administered samples and five heparin-administered samples were used.

Measurement

The results are shown in Table 7. As is obvious from this table, the reagents (1) and (2) of the present example showed lipase activity of 90 to 110% of that of the comparative example measured in the non-heparin-administered samples, but activity values of 52 to 69% of the lipase activity of the comparative example were obtained in the heparin-administered samples. The present example reveals that the effect can be attained no matter which of the R-1 and R-2 the bile acid is added to.

TABLE 7

|  | (A) Comparative example U/L | (B) Present example (1) U/L | (C) Present example (2) U/L | (B)/(A) % | (C)/(A) % |
|---|---|---|---|---|---|
| PRECIPATH ™ | 83.3 | 49.4 | 59.6 | 59.2 | 71.5 |
| PRECINORM ™ | 82.1 | 45.7 | 54.5 | 55.6 | 66.3 |
| Normal sample 41 | 75.8 | 79.1 | 81.3 | 104.3 | 107.3 |
| 42 | 129.8 | 127.7 | 125.3 | 98.4 | 96.5 |
| 43 | 39.7 | 42.7 | 41.1 | 107.6 | 103.5 |

TABLE 7-continued

|  | (A) Comparative example U/L | (B) Present example (1) U/L | (C) Present example (2) U/L | (B)/(A) % | (C)/(A) % |
|---|---|---|---|---|---|
| 44 | 99.6 | 95.0 | 96.8 | 95.4 | 97.2 |
| 45 | 47.2 | 49.7 | 46.0 | 105.3 | 97.3 |
| 46 | 43.7 | 44.5 | 41.5 | 102.0 | 95.0 |
| 47 | 38.0 | 40.1 | 39.5 | 105.5 | 103.8 |
| 48 | 26.8 | 24.1 | 28.1 | 90.0 | 104.7 |
| 49 | 32.9 | 33.4 | 29.7 | 101.4 | 90.1 |
| 50 | 39.5 | 42.7 | 42.3 | 108.1 | 107.1 |
| Heparin 51 | 76.6 | 46.8 | 51.2 | 61.1 | 66.9 |
| Heparin 52 | 109.5 | 65.7 | 67.5 | 60.0 | 61.6 |
| Heparin 53 | 93.3 | 60.5 | 64.0 | 64.9 | 68.6 |
| Heparin 54 | 73.4 | 38.2 | 44.3 | 52.1 | 60.4 |
| Heparin 55 | 82.1 | 49.3 | 54.5 | 60.0 | 66.3 |

(Example 16) Color Method

Preparation of Substrate

After weighing 1,2-dioleoyl glycerol (DODG) (manufactured by Nippon Fine Chemical Co., Ltd.) to attain a concentration of 13.95 mmol/L when dissolved, 1.2% polyoxyethylene (10) nonyl phenyl ether (NPE) (manufactured by Wako Pure Chemical Industries Ltd.) containing 2.5 mmol/L of MES (manufactured by Dojindo Laboratories) was added thereto to be dissolved therein by stirring at 37° C. for 4 hours, and the resultant was allowed to stand still in ice for 2 hours or more.

Reagent Composition

Controlled Example (R-1)

| 1.5 mmol/L | MES (pH 6.05) |
| 1.5 mmol/L | calcium chloride |
| 3 mmol/L | magnesium sulfate |
| 3 mmol/L | ATP |
| 1.05 mmol/L | 1,2-dioleoyl glycerol |
| 0.09% | NPE |
| 0.045% | N,N-bis(4-sulfobutyl)-3-methylaniline disodium (TODB) (manufactured by Dojindo Laboratories) |
| 90 U/L | glycerokinase (GKZ) (manufactured by Asahi Kasei Pharma Corporation) |
| 90 U/L | monoglyceride lipase (MGLPII) (manufactured by Asahi Kasei Pharma Corporation) |
| 3200 U/L | glycerol-3-phosphate oxidase (GPOM) (manufactured by Asahi Kasei Pharma Corporation) |
| 2250 U/L | peroxidase (manufactured by Sigma) |

(R-2)

| 150 mmol/L | TAPS (pH 8.1) |
| 3 mmol/L | 4-aminoantipyrine |
| 30 mmol/L | sodium deoxycholate |
| 36000 U/L | colipase |

As the present example, three types of reagents were prepared. Merely differences from the aforementioned comparative example will be described as follows:

Example 16-1

(R-1)

The following components were further added to the components of the above-described (R-1) of the comparative example:

| 12 mmol/L | sodium taurodeoxycholate |
| 12 mmol/L | sodium glycodeoxycholate |

(R-2)

| 150 mmol/L | BES (pH 7.0) |
| 3 mmol/L | 4-aminoantipyrine |
| 36000 U/L | colipase |

Example 16-2

(R-1) the Same Components as Those of the Comparative Example were Used (R-2)

| 150 mmol/L | BES (pH 7.0) |
| 3 mmol/L | 4-aminoantipyrine |
| 36000 U/L | colipase |
| 15 mmol/L | sodium taurodeoxycholate |
| 15 mmol/L | sodium glycodeoxycholate |

Example 16-3

(R-1)

The following component was further added to the components of the above-described (R-1) of the comparative example:

| 18000 U/L | colipase |

(R-2)

| 150 mmol/L | BES (pH 7.0) |
| 3 mmol/L | 4-aminoantipyrine |

-continued

| 15 mmol/L | sodium taurodeoxycholate |
| 15 mmol/L | sodium glycodeoxycholate |

Samples

PRECIPATH™, PRECINORM™, SERONORM™ lipid, five non-heparin-administered samples and nine heparin-administered samples were used.

Measurement was reduced. According to the present example, if the diglyceride and the colipase are contained in different reagents, the bile acid may be added to either of the first reagent and the second reagent as understood from the results obtained by the compositions (1) and (2). Alternatively, if the diglyceride and the bile acid are contained in different reagents, the colipase may be added to either of the reagents (as understood from the results obtained by the compositions (2) and (3)).

TABLE 9

|  | Liquitech U/L | Comparative example | Present example | | | Present example/ Comparative example | | |
| --- | --- | --- | --- | --- | --- | --- | --- | --- |
|  |  |  | (1) U/L | (2) | (3) | (1) % | (2) % | (3) % |
| PRECIPATH ™ | 110.1 | 122.0 | 119.5 | 129.9 | 130.4 | 97.9 | 106.4 | 106.9 |
| PRECINORM ™ | 38.8 | 44.9 | 44.0 | 45.1 | 44.9 | 98.1 | 100.6 | 100.1 |
| Pooled serum 1 | 36.6 | 39.4 | 36.4 | 39.6 | 39.6 | 92.3 | 100.4 | 100.4 |
| Pooled serum 2 | 22.3 | 16.9 | 15.4 | 17.9 | 16.8 | 91.6 | 106.0 | 99.4 |
| SERONORM ™ lipid | 6.8 | −1.2 | −2.0 | −2.4 | −2.4 | 168.6 | 203.3 | 204.6 |
| Non-heparin-administered 4 | 25.8 | 23.5 | 23.2 | 25.1 | 24.8 | 98.5 | 106.8 | 105.4 |
| 49 | 26.5 | 26.8 | 26.0 | 29.0 | 26.2 | 96.9 | 108.0 | 97.8 |
| 51 | 49.5 | 55.8 | 55.2 | 56.5 | 54.9 | 98.9 | 101.2 | 98.4 |
| 53 | 22.1 | 21.6 | 19.7 | 21.2 | 20.9 | 91.2 | 98.3 | 96.7 |
| 54 | 28.5 | 24.0 | 20.9 | 25.6 | 24.3 | 87.0 | 106.7 | 101.3 |
| 55 | 35.5 | 39.2 | 36.9 | 40.1 | 38.9 | 94.1 | 102.3 | 99.2 |
| 56 | 15.4 | 14.0 | 12.9 | 13.5 | 12.6 | 92.1 | 96.5 | 90.1 |
| 57 | 38.0 | 42.5 | 38.6 | 42.0 | 41.8 | 90.8 | 98.8 | 98.3 |
| 58 | 32.0 | 34.9 | 33.6 | 33.8 | 34.0 | 96.3 | 96.8 | 97.4 |
| Heparin 61 | 33.9 | 76.7 | 47.7 | 43.0 | 41.8 | 62.2 | 56.0 | 54.5 |
| Heparin 62 | 23.1 | 58.2 | 31.2 | 29.9 | 28.7 | 53.6 | 51.5 | 49.3 |
| Heparin 63 | 26.2 | 63.4 | 42.0 | 35.2 | 35.9 | 66.3 | 55.6 | 56.7 |
| Heparin 64 | 22.4 | 34.0 | 20.3 | 18.8 | 17.5 | 59.8 | 55.5 | 51.5 |
| Heparin 65 | 23.9 | 45.4 | 21.4 | 27.0 | 25.3 | 47.3 | 59.6 | 55.7 |
| Heparin 66 | 30.7 | 70.5 | 38.0 | 36.7 | 35.9 | 53.9 | 52.0 | 51.0 |
| Heparin 67 | 57.4 | 115.2 | 77.5 | 74.3 | 72.9 | 67.3 | 64.6 | 63.3 |

Table 8 shows a simple comparison table of the composition (1) of Example 16-1, the composition (2) of Example 16-2 and the composition (3) of Example 16-3. It is noted that a mixing ratio among the sample, the R-1 and the R-2 were 3:160:80.

TABLE 8

|  | (1) | (2) | (3) |
| --- | --- | --- | --- |
| R-1 | Substrate Bile acid | Substrate | Substrate Colipase |
| R-2 | Colipase | Bile acid Colipase | Bile acid |

Figure 17:
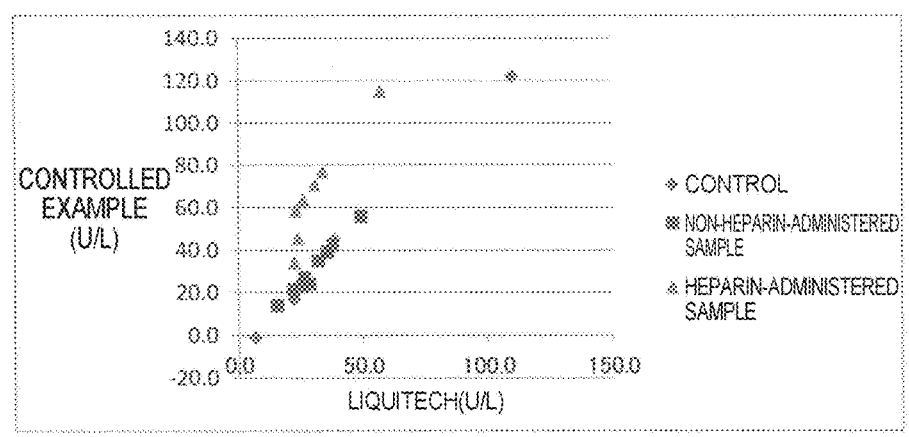
FIG. 17 is a correlation diagram between a measured value of human pancreatic lipase activity obtained by a comparative example in Example 16 and a measured value of the human pancreatic lipase activity obtained by "Liquitech Lipase Color II".
Figure 18:
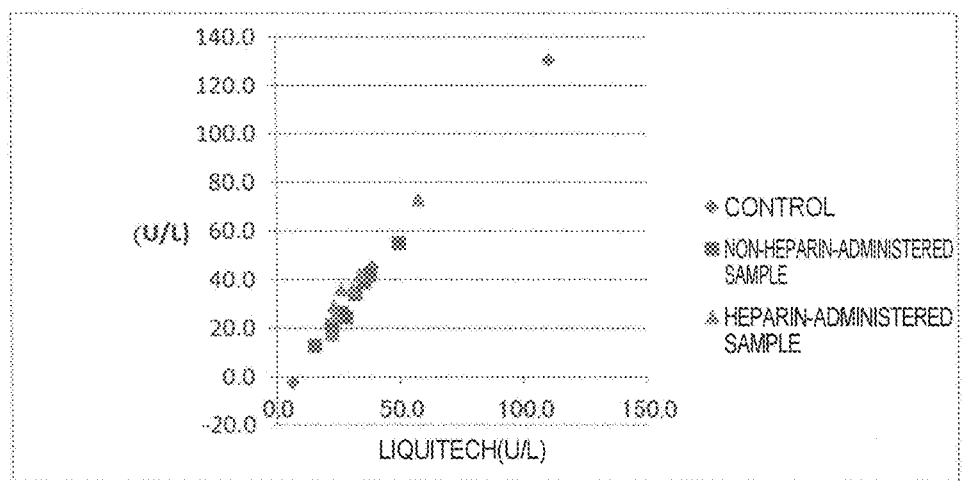
FIG. 18 is a correlation diagram between a measured value of the human pancreatic lipase activity according to Example 16-3 and a measured value of the human pancreatic lipase activity obtained by "Liquitech Lipase Color II".

A commercially available reagent for a resorufin colorimetric method, "Liquitech Lipase Color II" manufactured by Roche Diagnostics using 1,2-O-dilauryl-rac-glycerol-3-glutaric acid-(6-methylresorufin)ester (DGGR) was used for verifying the effect. It is noted that for the reagents of the present example and the comparative example, the activity was calculated by using a provisional calibrator. The results are shown in Table 9. In the non-heparin-administered samples, the human pancreatic lipase activity measured in using the present example was 87 to 108% of, namely, substantially equivalent to, the activity measured in using the comparative example, but in the heparin-administered samples, the activity was lowered in a range of 47 to 68%, which reveals that the influence of the non-pancreatic lipase Besides, the correlation between "Liquitech Lipase Color II" and the comparative example is illustrated in FIG. 17. It is understood that measured values of the heparin-administered samples are largely deviated from the regression line of the non-heparin-administered samples as compared with those obtained by using Liquitech. On the contrary, in the correlation between "Liquitech Lipase Color II" and the present example as illustrated in FIG. 18, such deviation is improved, and the measured values of the heparin-administered samples are mostly on the regression line of the non-heparin-administered samples. Accordingly, it was revealed that the present example can reduce the influence of the non-pancreatic lipase in a heparin-administered sample.

(Example 17) Relationship Between pH for Giving Maximum Value of Human Pancreatic Lipase Activity and pH at the Time of Activity Measurement NaGDCA was selected as the conjugated bile acid, NaCDCA was selected as the non-conjugated bile acid, and reaction solutions similar to those of Example 2 were used. The concentrations of NaGDCA and NaCDCA in the R-1 were respectively set to 16 mmol/L and 24 mmol/L, and the pH for giving a maximum value of the human pancreatic lipase activity at these concentrations was found to be about 7.6.

Next, this composition was used, with pH adjusted to 7.1 and 7.6, to perform measurement on control samples (controls each containing a pancreatic lipase) including two heparin-administered samples. At the same time, the measurement was performed by using the composition of the present example containing NaGDCA and NaTDCA (both in 20 mmol/L in the R-1) (MES buffer, pH 6.2). The molecular extinction coefficient of the reduced NADP was used to calculate the enzyme activity. The sensitivity in a pooled serum containing a human pancreatic LP recombinant attained by the combination of NaGDCA and NaCDCA was approximately 80% at pH 7.1 on the assumption that the sensitivity attained at pH 7.6, that is, the optimum pH, was 100%. It was that a measured value obtained in a heparin-administered serum by using the combination of NaGDCA and NaTDCA and using the reaction solution of pH 6.2 reflects a human pancreatic lipase activity value not influenced by the non-pancreatic lipase activity, and measured values obtained by using the composition containing the combination of NaGDCA and NaCDCA at pHs 7.1 and 7.6 were respectively reduced by using a calibrator to evaluate the influence of the non-pancreatic lipase.

The results are shown in Table 10. The lipase measured values in heparin-administered samples were 182% and 137% in terms of a relative value at pH 7.6, but were 118% and 100% at pH 7.1, and thus, the influence of the non-pancreatic lipase was reduced. These results reveal that even if the pH for giving a maximum value of the human pancreatic lipase activity does not accord with pH at the time of the lipase activity measurement, the effect of the present example can be exhibited as long as the pH at the time of the lipase activity measurement is 7.4 or lower. Besides, if the pH at the time of the lipase activity measurement was 7.6, the relative value (%) exceeded 120%, and therefore, it was revealed that this measurement was influenced by the non-pancreatic lipase by 20% or more.

(Example 18) Relationship Between pH for Giving Maximum Value of Human Pancreatic Lipase Activity and pH at the Time of Activity Measurement In the present example, NaTDCA was selected as the conjugated bile acid, NaDCA was selected as the non-conjugated bile acid, and reaction solutions similar to those of Example 2 were used. The concentrations of NaTDCA and NaDCA in the R-1 were respectively set to 27 mmol/L and 13 mmol/L, and the pH for giving a maximum value of the human pancreatic lipase activity at these concentrations was found to be about pH 7.55.

Next, this composition was used, with pH adjusted to 7.1, 7.55 and 7.75, to perform the measurement on control samples (controls each containing a pancreatic lipase) including two heparin-administered samples. In the same manner as in Example 17, the composition of the present example containing NaGDCA and NaTDCA (both in 20 mmol/L in the R-1) (MES buffer, pH 6.2) was subjected to the measurement to evaluate the sensitivity and the influence in the same manner as in Example 17.

The results are shown in Table 11. The sensitivity in a pooled serum containing a human pancreatic LP recombinant attained by a 2:1 mixture of NaTDCA and NaDCA was approximately 83% at pH 7.1 on the assumption that the sensitivity attained at pH 7.55, that is, the optimum pH, was 100%. On the other hand, the lipase measured values in heparin-administered samples were, in terms of a relative value, 258.9% and 244.5%, and 156.3% and 168.2% respectively at pHs 7.75 and 7.55, but were 109.4% and 103.0% at pH 7.1, and thus, the influence of the non-pancreatic lipase was reduced.

Similarly to the results of Example 17, these results reveal that even if the pH for giving a maximum value of the human pancreatic lipase activity does not accord with pH at the time of the lipase activity measurement, the effect of the present example can be exhibited as long as the pH at the time of the lipase activity measurement is 7.4 or lower. Besides, if the pH at the time of the lipase activity measurement was 7.55, the relative value (%) exceeded 120%, and therefore, it was revealed that this measurement was influenced by the non-pancreatic lipase by 20% or more.

TABLE 10

|  | Reference value | Measured value | | | | | Reduced value | | Reduced value/Reference value (%) | |
| --- | --- | --- | --- | --- | --- | --- | --- | --- | --- | --- |
| Conjugated bile acid | NaGDCA NaTDCA | NaGDCA | | | | | NaGDCA | | NaGDCA | |
| Non-conjugated bile acid |  | NaCDCA | | | | | NaCDCA | | NaCDCA | |
|  | pH 6.2 U/L | pH 7.1 U/L | pH 7.6 U/L | | | | pH 7.1 U/L | pH 7.6 U/L | pH 7.1 % | pH 7.6 % |
| Human pancreatic lp recombinant-containing serum | 180.8 | 130.8 | 163.1 | | | | 180.8 | 180.8 | 100.0 | 100.0 |
| PRECIPATH ™ | 110.7 | 78.2 | 97.2 | | | | 108.1 | 107.7 | 97.6 | 97.3 |
| PRECINORM ™ | 46.8 | 33.5 | 40.3 | | | | 46.4 | 44.6 | 99.0 | 95.3 |
| Pooled serum 1 | 42.1 | 29.4 | 35.9 | | | | 40.6 | 39.8 | 96.5 | 94.6 |
| Pooled serum 2 | 22.8 | 14.9 | 17.7 | | | | 20.6 | 19.6 | 90.2 | 85.8 |
| Heparin 71 | 31.3 | 26.8 | 51.4 | | | | 37.0 | 57.0 | 118.3 | 182.0 |
| Heparin 72 | 50.8 | 37.1 | 62.9 | | | | 51.3 | 69.7 | 101.0 | 137.2 |

TABLE 11

| | Reference value | Measured value | | | | Reduced value | | | Reduced value/Reference value (%) | | |
|---|---|---|---|---|---|---|---|---|---|---|---|
| Conjugated bile acid | NaGDCA NaTDCA | NaTDCA | | | | NaTDCA | | | NaTDCA | | |
| Non-conjugated bile acid | | NaDCA | | | | NaDCA | | | NaDCA | | |
| | pH 6.2 U/L | pH 7.1 U/L | pH 7.55 U/L | pH 7.75 U/L | | pH 7.1 U/L | pH 7.55 U/L | pH 7.75 U/L | pH 7.1 % | pH 7.55 % | pH 7.75 % |
| Human pancreatic lp recombinant-containing serum | 180.8 | 204.8 | 247.5 | 238.7 | | 180.8 | 180.8 | 180.8 | 100.0 | 100.0 | 100.0 |
| PRECIPATH ™ | 110.7 | 122.5 | 147.5 | 142.7 | | 108.1 | 107.7 | 108.1 | 97.6 | 97.3 | 97.6 |
| PRECINORM ™ | 46.8 | 52.5 | 61.1 | 61.2 | | 46.4 | 44.6 | 46.4 | 99.0 | 95.3 | 99.0 |
| Pooled serum 1 | 42.1 | 46.0 | 54.5 | 53.6 | | 40.6 | 39.8 | 40.6 | 96.5 | 94.6 | 96.5 |
| Pooled serum 2 | 22.8 | 23.3 | 26.8 | 27.2 | | 20.6 | 19.6 | 20.6 | 90.2 | 85.8 | 90.2 |
| Heparin 71 | 31.3 | 38.8 | 67.0 | 107.0 | | 34.2 | 48.9 | 81.0 | 109.4 | 156.3 | 258.9 |
| Heparin 72 | 50.8 | 59.3 | 117.0 | 164.0 | | 52.3 | 85.4 | 124.2 | 103.0 | 168.2 | 244.5 |

(Example 19) Comparison of Non-Conjugated Bile Acid and Salt Thereof

Figure 19:
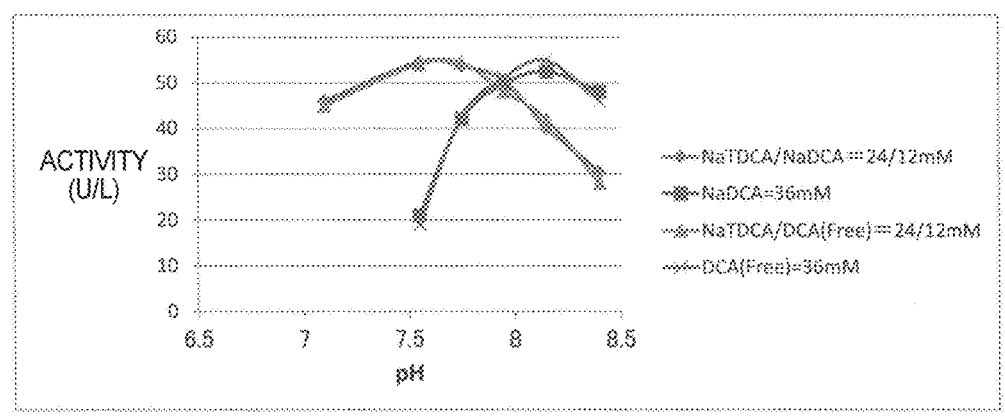
FIG. 19 is a graph illustrating that a difference between a non-conjugated bile acid and a sodium salt thereof does not influence the pH dependence of the human pancreatic lipase activity according to Example 19.

With respect to a combination of taurodeoxycholic acid and a deoxycholic acid, a reagent was prepared by using deoxycholic acid (DCA), that is, a non-conjugated bile acid, instead of sodium deoxycholate used in Example 3. The taurodeoxycholic acid was fixed in the form of a sodium salt. As illustrated in FIG. 19, if the proportion between the taurodeoxycholic acid and the deoxycholic acid was set to 24/12 mmol/L and 0/36 mmol/L, there was no difference in the obtained results between a case where the sodium salt was used and a case where the non-conjugated acid was used. Accordingly, it was revealed that the measurement of the human pancreatic lipase activity of the present example was not affected whether or not a used bile acid is in the form a salt.

INDUSTRIAL APPLICABILITY

The present invention can provide a measurement method for human pancreatic lipase activity in a sample in which the influence of a non-pancreatic lipase is reduced and high reproducibility is exhibited, and can be used for measurement of a human pancreatic lipase as a diagnostic marker for a pancreatic disease such as acute pancreatitis.

The invention claimed is:

1. A measurement method for human pancreatic lipase activity in a blood sample, comprising:
   1) maximizing the activity of human pancreatic lipase in the blood sample and decreasing the activity of human non-pancreatic lipase in the blood sample by bringing a bile acid that makes a pH for giving a maximum value of the human pancreatic lipase activity to be lower than 7.7, a diglyceride and a colipase into contact with the sample at pH 7.4 or lower; and
   2) detecting a signal amount varying in accordance with the human pancreatic lipase activity in the sample,
   wherein the bile acid is a bile acid comprising:
      a) at least one a-type bile acid which is glycodeoxycholic acid (GDCA), glycochenodeoxycholic acid (GCDCA), taurodeoxycholic acid (TDCA), taurochenodeoxycholic acid (TCDCA), or a salt thereof; and/or
      b) at least one b-i-type bile acid which is glycocholic acid (GCA), glycoursodeoxycholic acid (GUDCA), taurocholic acid (TCA), tauroursodeoxycholic acid (TUDCA), or a salt thereof, and at least one b-2-type bile acid which is deoxycholic acid (DCA), chenodeoxycholic acid (CDCA), or a salt thereof, and
   wherein when the bile acid(s) of a) is used, an addition rate of the a-type bile acid(s) is 40% or more based on a total amount of all bile acids and/or salts thereof.

2. The measurement method according to claim 1, wherein the bile acid(s) of a) is used in said contact.

3. The measurement method according to claim 1, wherein the bile acid(s) of b) is used in said contact.

4. The measurement method according to claim 1, wherein the a-type bile acid(s) is glycodeoxycholic acid (GDCA), GDCA and a salt thereof, a salt of GDCA, or two salts of GDCA.

5. The measurement method according to claim 1, wherein the a-type bile acid(s) is at least one of glycodeoxycholic acid (GDCA), taurodeoxycholic acid (TDCA), or salts thereof.

6. The measurement method according to claim 1, wherein the a-type bile acid(s) is taurodeoxycholic acid (TDCA)), TDCA and a salt thereof, a salt of TDCA, or two salts of TDCA.

7. The measurement method according to claim 1, wherein a non-ionic surface active agent is present together with the diglyceride.

8. The measurement method according to claim 7, wherein the non-ionic surface active agent is at least one of polyoxyethylene alkyl ether, polyoxyethylene alkyl phenyl ether, or polyoxyethylene secondary alcohol ether.

9. The measurement method according to claim 1, wherein a colorimetric method is employed in said detection.

10. The measurement method according to claim 1, wherein a concentration of all bile acids is ten times or more as high as a concentration of the diglyceride in terms of a molar ratio during said contact.

11. The measurement method according to claim 1, wherein the pH is 7.2 or lower during said contact.

12. The measurement method according to claim 1, wherein the blood sample is taken from an individual in need of diagnosis for pancreatic disease, and wherein the measurement method further comprises:
   3) diagnosing the individual in need of diagnosis of pancreatic disease as having pancreatic disease from the detected signal amount.

13. The measurement method according to claim 1, wherein the blood sample is contaminated with a human non-pancreatic lipase and is from a heparin-administered individual.

14. A measurement method for human pancreatic lipase activity in a blood sample, comprising:
1) maximizing the activity of human pancreatic lipase in the blood sample and decreasing the activity of human non-pancreatic lipase in the blood sample by bringing a bile acid, a diglyceride and a colipase into contact with the sample at pH 7.4 or lower; and
2) detecting a signal amount varying in accordance with the human pancreatic lipase activity in the sample,
wherein a concentration of the diglyceride is 0.35 to 2.5 mmol/L, and a concentration of the bile acid is ten to twenty times as high as the concentration of the diglyceride in terms of a molar ratio, and the bile acid is:
a) at least one a-type bile acid which is glycodeoxycholic acid (GDCA), glycochenodeoxycholic acid (GCDCA), taurodeoxycholic acid (TDCA), taurochenodeoxycholic acid (TCDCA), or salts thereof, a molar ratio of the a-type bile acid(s) being 40% or more based on a total amount of all bile acids and/or salts thereof; and/or
b) at least one b-i-type bile acid which is glycocholic acid (GCA), glycoursodeoxycholic acid (GUDCA), taurocholic acid (TCA), tauroursodeoxycholic acid (TUDCA), or salts thereof, and at least one b-2-type bile acid which is deoxycholic acid (DCA), chenodeoxycholic acid (CDCA), or salts thereof, a molar ratio of the b-1-type bile acid(s) being 30 to 70% based on the total amount of all the bile acids and/or salts thereof, and
wherein when the bile acid(s) of a) is used, an addition rate of the a-type bile acid(s) is 40% or more based on a total amount of all bile acids and/or salts thereof.

15. The measurement method according to claim 14, wherein the bile acid(s) of a) is used in said contact.

16. The measurement method according to claim 14, wherein the bile acid(s) of b) is used in said contact.

17. The measurement method according to claim 14, wherein the a-type bile acid(s) is glycodeoxycholic acid (GDCA), GDCA and a salt thereof, a salt of GDCA, or two salts of GDCA.

18. The measurement method according to claim 14, wherein the a-type bile acid(s) is at least one of glycodeoxycholic acid (GDCA), taurodeoxycholic acid (TDCA), or salts thereof.

19. The measurement method according to claim 14, wherein the a-type bile acid(s) is taurodeoxycholic acid (TDCA), TDCA and a salt thereof, a salt of TDCA, or two salts of TDCA.

20. The measurement method according to claim 14, wherein a non-ionic surface active agent is present together with the diglyceride.

21. The measurement method according to claim 20, wherein the non-ionic surface active agent is at least one of polyoxyethylene alkyl ether, polyoxyethylene alkyl phenyl ether, and polyoxyethylene secondary alcohol ether.

22. The measurement method according to claim 14, wherein a colorimetric method is employed in said detection.

23. The measurement method according to claim 14, wherein the pH is 7.2 or lower in said contact.

24. The measurement method according to claim 14, wherein the blood sample is taken from an individual in need of diagnosis for pancreatic disease, and wherein the measurement method further comprises:
3) diagnosing the individual in need of diagnosis of pancreatic disease as having pancreatic disease from the detected signal amount.

25. The measurement method according to claim 14, wherein the blood sample is contaminated with a human non-pancreatic lipase and is from a heparin-administered individual.

* * * * *